(12) United States Patent
Chen et al.

(10) Patent No.: US 11,874,110 B2
(45) Date of Patent: Jan. 16, 2024

(54) SELF-MIXING INTERFEROMETRY DEVICE CONFIGURED FOR NON-RECIPROCAL SENSING

(71) Applicant: Apple Inc., Cupertino, CA (US)

(72) Inventors: Tong Chen, Fremont, CA (US); Ahmet Fatih Cihan, San Jose, CA (US); Mingzhou Jin, Campbell, CA (US)

(73) Assignee: Apple Inc., Cupertino, CA (US)

( * ) Notice: Subject to any disclaimer, the term of this patent is extended or adjusted under 35 U.S.C. 154(b) by 292 days.

(21) Appl. No.: 17/118,394

(22) Filed: Dec. 10, 2020

(65) Prior Publication Data
US 2022/0099431 A1 Mar. 31, 2022

Related U.S. Application Data

(60) Provisional application No. 63/083,413, filed on Sep. 25, 2020.

(51) Int. Cl.
*G01B 9/02* (2022.01)
*G06F 3/01* (2006.01)
(Continued)

(52) U.S. Cl.
CPC ......... *G01B 9/02092* (2013.01); *G02F 1/093* (2013.01); *G02F 1/21* (2013.01); *G06F 3/017* (2013.01)

(58) Field of Classification Search
CPC ............ G01B 9/02092; G01B 9/02091; G01B 11/303; G02F 1/093; G02F 1/21; G06F 3/017; G06F 3/0304; A61B 5/0059
See application file for complete search history.

(56) References Cited

U.S. PATENT DOCUMENTS

| 4,254,333 A | 3/1981 | Bergström |
| 4,402,601 A | 9/1983 | Riva |

(Continued)

FOREIGN PATENT DOCUMENTS

| CN | 2163384 | 4/1994 |
| CN | 1279394 | 1/2001 |

(Continued)

OTHER PUBLICATIONS

U.S. Appl. No. 16/773,827, filed Jan. 27, 2020, Mutlu et al.
(Continued)

*Primary Examiner* — Hwa Andrew Lee
(74) *Attorney, Agent, or Firm* — Brownstein Hyatt Farber Schreck, LLP

(57) ABSTRACT

Methods and systems concerning non-reciprocal sensing paths for a self-mixing interferometry operation are disclosed herein. Optical components may be used to direct light transmit from a light source along an illumination path. The optical components may additionally return light to the light source after being reflected from a target and may direct the returned light along a collection path. The illumination path and the collection path may be at least partially non-reciprocal so that the transmitted light and the returned light follow along partially different paths. Once the received light is received within a cavity of the light source, a self-mixing interferometry operation may be performed and may be used to detect a property of the target in relation to the light source.

17 Claims, 23 Drawing Sheets

(51) Int. Cl.
*G02F 1/21* (2006.01)
*G02F 1/09* (2006.01)

(56) References Cited

U.S. PATENT DOCUMENTS

| | | | |
|---|---|---|---|
| 4,468,131 A | 8/1984 | Bui et al. | |
| 4,913,547 A | 4/1990 | Moran | |
| 5,500,708 A | 3/1996 | Ohsawa | |
| 5,748,295 A | 5/1998 | Farmer | |
| 5,781,297 A | 7/1998 | Castore | |
| 5,825,465 A * | 10/1998 | Nerin | G01P 3/366 356/28.5 |
| 6,233,045 B1 | 5/2001 | Suni et al. | |
| 6,531,767 B2 | 3/2003 | Shrauger | |
| 6,794,671 B2 | 9/2004 | Nicoli et al. | |
| 6,816,523 B1 | 11/2004 | Glenn et al. | |
| 6,872,931 B2 | 3/2005 | Liess et al. | |
| 7,139,446 B2 | 11/2006 | Slotwinski | |
| 7,184,445 B2 | 2/2007 | Guenter | |
| 7,277,180 B2 | 10/2007 | Townley-Smith et al. | |
| 7,336,368 B2 | 2/2008 | Liao et al. | |
| 7,366,217 B2 | 4/2008 | Guenter et al. | |
| 7,388,672 B2 | 6/2008 | Zhou et al. | |
| 7,509,050 B2 | 3/2009 | Ekkizogloy et al. | |
| 7,557,795 B2 | 7/2009 | Kong et al. | |
| 7,589,709 B2 | 9/2009 | Liess et al. | |
| 7,619,744 B2 | 11/2009 | Liess | |
| 7,620,332 B2 | 11/2009 | Nishiyama | |
| 7,667,851 B2 | 2/2010 | Dubois et al. | |
| 7,675,020 B2 | 3/2010 | Machida | |
| 7,684,957 B2 | 3/2010 | Ueno | |
| 7,990,521 B2 | 8/2011 | Ueno | |
| 7,995,193 B2 | 8/2011 | Kuwata | |
| 8,174,597 B2 | 5/2012 | Ogasawara | |
| 8,208,814 B2 | 6/2012 | Sheth et al. | |
| 8,248,615 B2 | 8/2012 | Ueno | |
| 8,339,584 B2 | 12/2012 | Christian et al. | |
| 8,378,287 B2 | 2/2013 | Schemmann et al. | |
| 8,405,902 B2 | 3/2013 | Irie | |
| 8,416,424 B2 | 4/2013 | Werner et al. | |
| 8,446,592 B1 | 5/2013 | Arissian | |
| 8,529,460 B2 | 9/2013 | Kawano et al. | |
| 8,532,751 B2 | 9/2013 | McKenna | |
| 8,625,099 B2 | 1/2014 | Sakamoto et al. | |
| 8,736,581 B2 | 5/2014 | Han et al. | |
| 8,751,091 B2 | 6/2014 | Moench et al. | |
| 8,781,687 B2 | 7/2014 | Han et al. | |
| 8,820,147 B2 | 9/2014 | Sinha | |
| 8,896,745 B2 | 11/2014 | Takachi | |
| 8,942,069 B2 | 1/2015 | Tortora | |
| 8,982,336 B2 | 3/2015 | Ueno | |
| 9,004,698 B2 | 4/2015 | Kilcher et al. | |
| 9,091,573 B2 | 7/2015 | Van Der Lee et al. | |
| 9,091,747 B2 | 7/2015 | Pruijmboom | |
| 9,146,304 B2 | 9/2015 | Land et al. | |
| 9,160,390 B2 | 10/2015 | Zhou et al. | |
| 9,229,024 B2 | 1/2016 | Carpaij et al. | |
| 9,354,315 B2 | 5/2016 | Lepaysan et al. | |
| 9,397,476 B2 | 7/2016 | Baier et al. | |
| 9,420,155 B2 | 8/2016 | Brodie | |
| 9,459,352 B2 | 10/2016 | Becker et al. | |
| 9,588,586 B2 | 3/2017 | Rihn | |
| 9,648,221 B2 | 5/2017 | Seo et al. | |
| 9,658,113 B2 | 5/2017 | Bosch et al. | |
| 9,677,986 B1 | 6/2017 | Baldwin et al. | |
| 9,703,173 B2 | 7/2017 | Brodie | |
| 9,726,474 B2 | 8/2017 | Royo Royo | |
| 9,759,736 B2 | 9/2017 | Zamama et al. | |
| 9,772,398 B2 | 9/2017 | Bikumandla et al. | |
| 9,778,037 B2 | 10/2017 | Bestler | |
| 9,778,177 B2 | 10/2017 | Roke et al. | |
| 9,911,890 B2 | 3/2018 | Renard et al. | |
| 9,912,923 B2 | 3/2018 | Kilcher et al. | |
| 9,952,245 B2 | 4/2018 | Ueno | |
| 9,995,877 B2 | 6/2018 | Nakamura | |
| RE46,930 E | 7/2018 | Mimeault | |
| 10,070,799 B2 | 9/2018 | Ang et al. | |
| 10,180,397 B2 | 1/2019 | Rakic | |
| 10,184,783 B2 | 1/2019 | Flanders et al. | |
| 10,215,555 B2 | 2/2019 | Chen et al. | |
| 10,222,474 B1 | 3/2019 | Raring et al. | |
| 10,317,651 B2 | 6/2019 | Furutake et al. | |
| 10,379,028 B2 | 8/2019 | Spruit et al. | |
| 10,386,554 B2 | 8/2019 | Hjelmstrom et al. | |
| 10,390,730 B1 | 8/2019 | Shoeb | |
| 10,492,679 B2 | 12/2019 | Zhou | |
| 10,503,048 B2 | 12/2019 | Del Bino et al. | |
| 10,555,079 B2 | 2/2020 | Bakish | |
| 10,613,625 B2 | 4/2020 | Huang et al. | |
| 10,614,295 B2 | 4/2020 | Kim et al. | |
| 10,635,800 B2 | 4/2020 | Bakish | |
| 10,581,474 B1 | 6/2020 | Fishman et al. | |
| 10,705,211 B2 | 7/2020 | Jacobs et al. | |
| 10,718,922 B2 | 7/2020 | Yong et al. | |
| 10,788,308 B2 | 9/2020 | Mutlu et al. | |
| 10,791,283 B2 | 9/2020 | Bardagjy et al. | |
| 10,824,275 B2 | 11/2020 | Mutlu et al. | |
| 10,845,873 B2 | 11/2020 | Huang | |
| 10,866,083 B2 | 12/2020 | Van Der Lee et al. | |
| 10,871,820 B2 | 12/2020 | Mutlu et al. | |
| 10,871,836 B2 | 12/2020 | Dashevsky | |
| 10,970,556 B2 | 4/2021 | Teich et al. | |
| 11,054,244 B2 | 7/2021 | Ouweltjes | |
| 11,073,615 B2 | 7/2021 | Chua et al. | |
| 11,112,233 B2 | 9/2021 | Mutlu et al. | |
| 11,112,235 B2 | 9/2021 | Mutlu et al. | |
| 11,119,021 B2 | 9/2021 | Spruit et al. | |
| 11,150,332 B1 | 10/2021 | Chen et al. | |
| 11,156,456 B2 | 10/2021 | Chen et al. | |
| 11,157,113 B2 | 10/2021 | Winkler et al. | |
| 11,175,700 B1 | 11/2021 | Poole | |
| 11,187,643 B2 | 11/2021 | Jutte et al. | |
| 11,243,068 B1 | 2/2022 | Mutlu et al. | |
| 11,243,686 B2 | 2/2022 | McCord | |
| 11,280,714 B2 | 3/2022 | Momtahan et al. | |
| 11,409,365 B2 | 8/2022 | Mutlu et al. | |
| 11,419,546 B2 | 8/2022 | Cihan et al. | |
| 11,450,293 B2 | 10/2022 | Chen et al. | |
| 2005/0156874 A1 | 7/2005 | Kong | |
| 2005/0157971 A1 | 7/2005 | Juijve | |
| 2006/0239312 A1 | 10/2006 | Kewitsch et al. | |
| 2008/0123106 A1 | 5/2008 | Zeng et al. | |
| 2009/0002829 A1 | 1/2009 | Shinohara | |
| 2011/0126617 A1 | 6/2011 | Bengoechea Apezteguia et al. | |
| 2011/0267467 A1 | 11/2011 | Kimura et al. | |
| 2012/0002189 A1 | 1/2012 | Bengoechea Apezteguia et al. | |
| 2012/0281221 A1 | 11/2012 | Studer et al. | |
| 2014/0293055 A1 | 10/2014 | Otsuka | |
| 2015/0309568 A1 | 10/2015 | Miki | |
| 2016/0021285 A1 | 1/2016 | Nadler et al. | |
| 2017/0090599 A1 | 3/2017 | Kuboyama et al. | |
| 2017/0192133 A1 | 7/2017 | Murakami et al. | |
| 2017/0343817 A1 | 11/2017 | Bietry | |
| 2018/0073924 A1 | 3/2018 | Steinmann et al. | |
| 2018/0081434 A1 | 3/2018 | Siddiqui et al. | |
| 2019/0146065 A1 | 5/2019 | Jutte et al. | |
| 2019/0285537 A1 | 9/2019 | Spruit et al. | |
| 2019/0285753 A1 | 9/2019 | Spruit et al. | |
| 2019/0317454 A1 | 10/2019 | Holenarsipur et al. | |
| 2019/0319157 A1 | 10/2019 | Coffy et al. | |
| 2019/0391539 A1 | 12/2019 | Perkins et al. | |
| 2020/0072723 A1 | 3/2020 | Weiss | |
| 2020/0072740 A1 | 3/2020 | Venturini et al. | |
| 2020/0103274 A1 | 4/2020 | Garrett et al. | |
| 2020/0200522 A1 | 6/2020 | Huang et al. | |
| 2020/0309661 A1 | 10/2020 | Spruit et al. | |
| 2020/0318945 A1 | 10/2020 | Mutlu et al. | |
| 2020/0319082 A1 | 10/2020 | Mutlu et al. | |
| 2020/0337631 A1 | 10/2020 | Sahin | |
| 2020/0370879 A1 | 11/2020 | Mutlu et al. | |
| 2020/0370886 A1 | 11/2020 | Chen et al. | |
| 2021/0003385 A1 | 1/2021 | Tan et al. | |
| 2021/0010797 A1 | 1/2021 | Cihan et al. | |
| 2021/0011559 A1 | 1/2021 | Mutlu et al. | |

(56) References Cited

U.S. PATENT DOCUMENTS

| | | |
|---|---|---|
| 2021/0015350 A1 | 1/2021 | Butte et al. |
| 2021/0080248 A1 | 3/2021 | Cihan et al. |
| 2021/0104873 A1 | 4/2021 | Gerlach |
| 2021/0116355 A1 | 4/2021 | Spruit et al. |
| 2021/0294489 A1 | 9/2021 | Li et al. |
| 2021/0302745 A1 | 9/2021 | Mutlu et al. |
| 2021/0364273 A1 | 11/2021 | Mutlu et al. |
| 2022/0003543 A1 | 1/2022 | Chen et al. |
| 2022/0099431 A1 | 3/2022 | Chen et al. |
| 2022/0099436 A1 | 3/2022 | Chen et al. |
| 2022/0155052 A1 | 5/2022 | Mutlu et al. |
| 2022/0202515 A1 | 6/2022 | Itkowitz et al. |
| 2022/0244041 A1 | 8/2022 | Chen et al. |
| 2022/0404138 A1 | 12/2022 | Mutlu et al. |
| 2023/0087691 A1 | 3/2023 | Chen et al. |

FOREIGN PATENT DOCUMENTS

| | | | |
|---|---|---|---|
| CN | 1682105 | 10/2005 | |
| CN | 101592762 | 12/2009 | |
| CN | 102109650 | 6/2011 | |
| CN | 102564909 | 7/2012 | |
| CN | 103733061 | 4/2014 | |
| CN | 105223579 | 1/2016 | |
| CN | 106226783 | 12/2016 | |
| CN | 107564924 | 1/2018 | |
| CN | 207231962 | 4/2018 | |
| CN | 108225543 | 6/2018 | |
| CN | 109154659 | 1/2019 | |
| CN | 108692663 B | * 4/2020 | ............ G01B 11/02 |
| EP | 3796140 | 3/2021 | |
| GB | 2443662 | 5/2008 | |
| JP | H06331745 | 12/1994 | |
| JP | 2005528682 | 9/2005 | |
| JP | 2010526315 | 7/2010 | |
| JP | 2011523700 | 8/2011 | |
| JP | 2013508717 | 3/2013 | |
| JP | 2019515258 | 6/2019 | |
| JP | 2019121691 | 7/2019 | |
| WO | WO 05/013517 | 2/2005 | |
| WO | WO 09/156937 | 12/2009 | |
| WO | WO 10/058322 | 5/2010 | |
| WO | WO 10/139144 | 12/2010 | |
| WO | WO 12/049561 | 4/2012 | |
| WO | WO 14/086375 | 6/2014 | |
| WO | WO 17/178711 | 10/2017 | |
| WO | WO 17/198699 | 11/2017 | |
| WO | WO 18/036685 | 3/2018 | |
| WO | WO 18/104153 | 6/2018 | |
| WO | WO 18/104154 | 6/2018 | |
| WO | WO 18/206474 | 11/2018 | |
| WO | WO 19/015623 | 1/2019 | |
| WO | WO 19/042953 | 3/2019 | |
| WO | WO 20/207908 | 10/2020 | |
| WO | WO 21/257737 | 12/2021 | |

OTHER PUBLICATIONS

U.S. Appl. No. 16/827,646, filed Mar. 23, 2020, Li et al.
U.S. Appl. No. 16/917,891, filed Jun. 30, 2020, Chen et al.
U.S. Appl. No. 17/124,132, filed Dec. 16, 2020, Chen et al.
U.S. Appl. No. 17/167,218, filed Feb. 4, 2021, Shou et al.
U.S. Appl. No. 17/710,682, filed Mar. 31, 2022, Chen et al.
Diao et al., "High-speed high-resolution heterodyne interferometer using a laser with low beat frequency," Applied Optics, vol. 55, No. 1, 2015, pp. 110-116.
Author Unknown, "Biometric Technology Market Foresees Growth due to Innovative Advancement," https://menafn.com/mf_contact.aspx?src=Contact_Authors, Dec. 18, 2020, 2 pages.
Guiliani et al., "Laser diode self-mixing technique for sensing applications," Journal of Optics A: Pure and Applied Optics, 2002, S283-S294.

* cited by examiner

SELF-MIXING INTERFEROMETRY DEVICE CONFIGURED FOR NON-RECIPROCAL SENSING

CROSS-REFERENCE TO RELATED APPLICATION

This application is a nonprovisional of and claims the benefit under 35 U.S.C. § 119(e) of U.S. Provisional Patent Application No. 63/083,413, filed Sep. 25, 2020, the contents of which are incorporated herein by reference as if fully disclosed herein.

FIELD

Embodiments described herein generally relate to structures and configurations of self-mixing interferometry (SMI) sensors that may be used to detect, measure, or determine an object location, speed, velocity, distance, motion, and/or displacement. In particular, described embodiments may relate to an SMI sensor configured to perform non-reciprocal sensing.

BACKGROUND

Electronic devices may be provided with various kinds of sensors for sensing an internal or external environment of the electronic device. Internal sensing may be used to detect, for example, a user input, whereas external sensing may be used to detect, for example, a property of the device's user (e.g., a user biometric).

SUMMARY

In some embodiments, an apparatus for performing non-reciprocal self-mixing interferometry may comprise a self-mixing interferometry sensor configured to emit a beam of light and a birefringent circulator positioned over an aperture of the light source. The birefringent circulator may be configured to direct the beam of light emitted from the self-mixing interferometry sensor along an illumination path and to direct a returned portion of the beam of light, received along a collection path different from the illumination path, back toward the light source.

A birefringent circulator may comprise a Faraday rotator and a wave plate. The Faraday rotator and the wave plate may be configured to transform a first polarization of the beam of light into a second polarization as the beam of light travels along the illumination path. The Faraday rotator and the wave plate may be further configured to keep a third polarization of the returned portion of the beam of light unchanged as the returned portion of the beam of light is directed back toward the light source. In some embodiments, the wave plate may be a half-wave plate with an optical axis aligned to the first polarization.

A first angle of the beam of light, as the beam of light leaves the birefringent circulator along the illumination path, may be different than a second angle of the returned portion of the beam of light, as the returned portion of the beam of light enters the birefringent circulator along the collection path.

In some embodiments, a first polarization of the beam of light before the beam of light enters the birefringent circulator may be p-polarization and a second polarization of the beam of light after the beam of light exits the birefringent circulator may be s-polarization.

In some embodiments, a third polarization of the returned portion of the beam of light before the returned portion of the beam of light enters the birefringent circulator may be p-polarization and a fourth polarization of the returned portion of the beam of light after the returned portion of the beam of light exits the birefringent circulator may be p-polarization.

In some embodiments, the birefringent circulator may have a first refractive index in a first direction of travel along the illumination path. The birefringent circulator may further have a second refractive index in a second direction of travel along the collection path. The first refractive index may be different from the second refractive index. In some embodiments, the illumination path and the collection path may be focused on a common detection space.

In some embodiments, an electronic device for performing non-reciprocal self-mixing interferometry may comprise a self-mixing interferometry sensor configured to emit a beam of light and a birefringent circulator positioned in an illumination path of the emitted beam of light and in a collection path of a returned portion of the beam of light. The birefringent circulator may be configured to direct the beam of light emitted from the self-mixing interferometry sensor from a first aperture of the birefringent circulator and to direct a returned portion of the beam of light, received from a second aperture of the birefringent circulator, into the self-mixing interferometry sensor.

In some embodiments, the beam of light directed from the first aperture may be configured to travel along a curved path underneath a target and the returned portion of the beam of light may exit the curved path from under the target.

In some embodiments, a processing unit may be configured to determine, from an output of the self-mixing interferometry sensor, a displacement or a movement of a sub-surface feature of an object.

An electronic device may further comprise a gesture recognizer configured to receive a self-mixing interferometry signal from the self-mixing interferometry sensor and determine a gesture of the user based on the received self-mixing interferometry signal.

The gesture recognizer may be further configured to apply a frequency domain analysis to the self-mixing interferometry signal and may determine the gesture of the user based on the change in at least one property of the operational parameter of the self-mixing interferometry signal, as determined by the frequency domain analysis.

The electronic device may be at least one of an electronic watch or a mobile phone.

In some embodiments, an electronic device may comprise a self-mixing interferometry sensor comprising a light emitter configured to emit a beam of light and a photodetector configured to receive a returned portion of the beam of light. The electronic device may further comprise a set of one or more optical components positioned over an aperture of the light emitter. The set of one or more optical components may define a first optical path configured to propagate the emitted beam of light between a first receiving location and a first emission location and a second optical path configured to propagate the returned portion of the beam of light between a second receiving location and a second emission location. The first optical path may be different from the second optical path.

In some embodiments, the set of one or more optical components may comprise a first birefringent wedge, a second birefringent wedge, and a Faraday rotator positioned between the first birefringent wedge and the second birefringent wedge.

The set of one or more optical components may further comprise a lens configured to collimate the beam of light as the beam of light enters the set of one or more optical components. The set of one or more optical components may further comprise a half-wave plate positioned between the Faraday rotator and the second birefringent wedge. In some embodiments, the set of one or more optical components may be a passive, non-reciprocal meta-structure.

BRIEF DESCRIPTION OF THE DRAWINGS

Reference will now be made to representative embodiments illustrated in the accompanying figures. It should be understood that the following descriptions are not intended to limit the embodiments to one or more preferred embodiments. To the contrary, they are intended to cover alternatives, modifications, and equivalents as may be included within the spirit and scope of the described embodiments as defined by the appended claims. Identical reference numerals have been used, where possible, to designate identical features that are common to the figures.

Figure 1A:
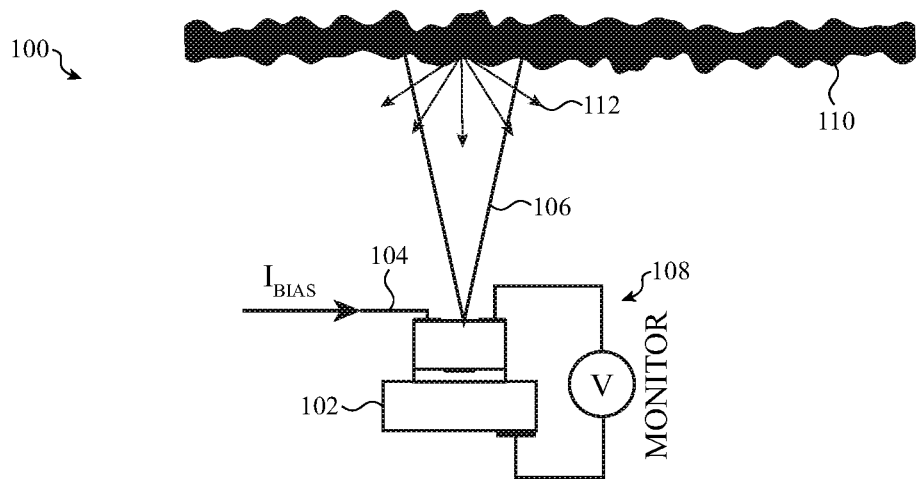
FIG. 1A depicts a vertical cavity surface emitting laser (VCSEL) diode used to transmit a beam of light toward a target.

The use of cross-hatching or shading in the accompanying figures is generally provided to clarify the boundaries between adjacent elements and to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof), and the boundaries, separations, and positional relationships presented therebetween, are provided in the accompanying figures merely to facilitate an understanding of the various embodiments described herein, may not necessarily be presented or illustrated to scale, and are not intended to indicate any preference or requirement for an illustrated embodiment to the exclusion of embodiments described with reference thereto.

DETAILED DESCRIPTION

The following disclosure relates to self-mixing interferometry sensors such as may be used as, for example, touch, biometric, and/or input sensors. In particular, a self-mixing interferometry sensor may utilize and/or include a set of one or more optical components to create non-reciprocal light paths to transmit and receive light with respect to a light source (e.g., a laser light emitter). As used herein, a self-mixing interferometry sensor may include a light source and/or a photodetector. For example, self-mixing interferometry sensors may use vertical cavity surface emitting laser (VCSEL) diodes, as a non-limiting example of a light source, and associated resonance cavity photodetectors (RCPDs), as a non-limiting example of a photodetector. An electronic device may use a self-mixing interferometry sensor as part of detecting, for example, a presence, proximity, size, displacement, distance, motion, speed, or velocity of surface or subsurface features of a target. In accordance with the provided disclosure, a self-mixing interferometry sensor may additionally be used to measure physical properties of surface or subsurface features. For example, a self-mixing interferometry sensor may be used to measure surface or subsurface reflectivity; microstructure texture and/or roughness; a particle density and/or size; a polarization state; and so on. As used herein, the phrase "target" may be used to refer to any structure toward which a self-mixing interferometry sensor transmits light for the purpose of sensing one or more parameters of the targets. As used herein, targets may include various input surfaces or objects. Hereinafter, for convenience, all possible measured parameters will be referred to as "detected properties."

Such self-mixing interferometry sensors detect the detected properties of a target by causing one or more light sources (e.g., a laser light emitter) to emit a beam of phase-coherent light (e.g., a laser light) toward the target by applying a forward bias and by receiving a returned portion of the emitted beam of phase-coherent light back into a cavity of the light source component of the self-mixing interferometry sensor. A beam of phase-coherent light emitted from the light source may be referred to as transmitted light or a transmitted beam of light. The transmitted light may be returned (e.g., reflected or scattered) from the target and may be received back into a cavity of the light source and/or the self-mixing interferometry sensor. As used herein, returned light may include light reflected and/or scattered from a target and may be referred to as a returned portion of a beam of light, a returned beam of light, returned light, received light, and/or a received beam of light.

The returned light received by the self-mixing interferometry sensor may result in a self-mixing interference operation in which a first optical frequency of emitted light may be different than a second optical frequency of returning light. Self-mixing interference between intra-cavity light and returning light may result in a beating radio frequency that is equal to the difference between the first and the second optical frequencies. The beating radio frequency may be measured and/or analyzed and may correspond to the detected properties of the target.

In some embodiments, the target may have strongly retro-reflective components and may result in a large, or entire, portion of the returned light being directed back to the self-mixing interferometry sensor. In these embodiments, the retro-reflective components may result in a strong self-mixing signal, with respect to noise from, for example, aggressor circuitry, and a high degree of accuracy for detected properties may be obtained. In some embodiments, a strength of a self-mixing signal may be configured to be below a threshold value, as a self-mixing signal that is above the threshold value may interfere with operations of an associated light source.

In some embodiments, the target may be reflective and/or otherwise not strongly retro-reflective. However, in instances where the target is not strongly retro-reflective, the reflected light may be scattered in a large number of directions and the light source of the self-mixing interferometry sensor may receive an insufficient portion of the returned light. In these situations, a self-mixing interference operation may result in readings that inaccurately or irregularly correspond to the detected properties of the target. For example, a returned beam of light may be reflected at an angle different than an angle of incidence for the transmitted beam of light, resulting in an insufficient portion of the returned beam of light returning to the self-mixing interferometry sensor. To ensure that portions of such returned beams of light do sufficiently return to the self-mixing interferometry sensor, non-reciprocal optics may be provided as discussed herein.

In some embodiments, an optical circulator may be provided between a light source and a target. The optical circulator may include optical elements such that at least a portion of a transmitted beam of light follows along a path different from at least a portion of a returned beam of light. In some examples, the respective beams of light may enter or exist at different locations on an optical circulator. In this way, returned light may be collected and directed back toward the light source even if reflected at an angle different than an angle of incidence for the transmitted beam of light. As used herein, the optical circulator may be referenced as an optical component.

In some embodiments, an optical circulator may be defined as a multi-port (e.g., more than two ports) non-reciprocal component configured to transmit beams of light to different ports based on properties of the beams of light (e.g., a polarization or a wavelength). In some embodiments, an optical circulator may be a birefringent circulator and may include at least one birefringent crystal. A birefringent circulator may be used to direct the transmitted beam of light of a certain polarization toward one location on the target and to collect the returned beam of light of the same polarization as originating from a second location on the target. For example, some types of targets may be partially transparent to certain forms of light. The light that penetrates the target may follow a multi-path scattering trajectory at or below a surface of the target. Light, including a mixture of light polarizations, may then scatter at or below a surface of the target at a departing position different than the initial incident position. Without an optical or birefringent circulator, the light, including various polarizations, scattered from the departing position may not be collected by the self-mixing interferometry sensor or may be overwhelmed by light reflected from undesired sensing locations. For example, if features below a surface of a target are desirably detected, light reflected from positions on the surface of the target may overwhelm the light reflected from below-surface features. In embodiments with an optical or birefringent circulator, the optical or birefringent circulator may assist in redirecting the returned light toward the self-mixing interferometry sensor or in rejecting light reflecting from positions on a surface of a target, in situations where below-surface features are desirably detected.

By using non-reciprocal light paths, self-mixing interferometry operations may be performed even in situations where the returned beam of light is not retro-reflectively directed back to the self-mixing interferometry sensor. In this way, self-mixing interferometry operations may be performed on, for example, partially transparent; irregular; rough; and/or reflective targets. In the event that the transmitted beam of light fully or partially penetrates the target, objects below the top surface of the target (e.g., sub-surface targets) may be detected due to a lack of interference between the transmitted and returned light paths.

These and other embodiments are discussed with reference to FIGS. 1A-10. However, those skilled in the art will readily appreciate that the detailed description given herein with respect to these figures is for explanatory purposes only and should not be construed as limiting.

FIG. 1A depicts a self-mixing interferometry system 100 that uses a VCSEL 102 configured to transmit a beam of light 106 toward a target 110. In the embodiment depicted in FIG. 1A, the beam of light 106 may be emitted in a cone (e.g., the light expands as it extends past the VCSEL 102). In some embodiments, the beam of light 106 may be substantially collimated or focused via, for example, a lens. The VCSEL 102 may emit the beam of light 106 under a forward current bias. To impart the forward current bias $I_{BIAS}$ 104, a bias voltage may be supplied to the VCSEL 102. In this way, a laser light emission (e.g., a beam of light) from the VCSEL 102 may be induced.

The beam of light 106 may be reflected from the target 110 as a number of reflections 112. The target 110 may be reflective and/or diffusively reflective and may return the reflections 112 along any angle and/or direction. In some examples, a portion of the reflections 112 may be redirected back into the VCSEL 102 while another portion may be reflected away from the VCSEL 102. In alternative or additional embodiments, the target 110 may be retro-reflective, or have partially retro-reflective properties, and may direct a majority of the reflections 112 back toward the VCSEL 102. As described herein, light returned back toward the VCSEL 102 may be referred to as returned light and/or returned beams of light and may include light reflected and/or scattered from the target 110 either as reflections 112 or otherwise.

Some, or all, of the reflections 112 may be received back into the VCSEL 102 and, in particular, into a lasing cavity of the VCSEL 102. Once received into the lasing cavity, a self-mixing interferometry operation may occur and a property of the beam of light 106 may be altered. In some embodiments, an electrical property of the VCSEL 102 may vary in response to a self-mixing interferometry operation. For example, a voltage monitor 108 may detect changes in a junction voltage of the VCSEL 102 that correlate with a distance or motion of the target 110, with respect to the VCSEL 102.

Figure 1B:
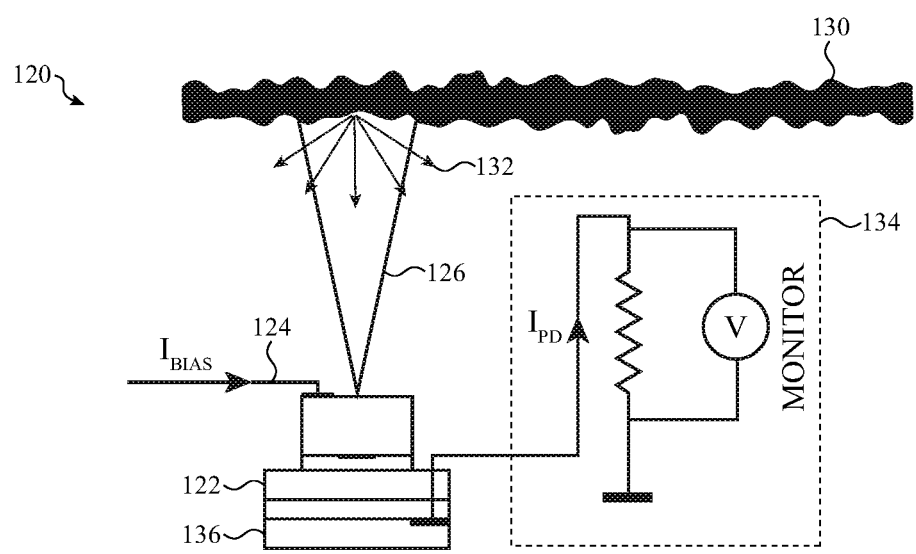
FIG. 1B depicts a VCSEL and an integrated photodetector used to emit a beam of light toward a target and to perform a self-mixing operation.

FIG. 1B depicts a self-mixing interferometry system 120 that uses a VCSEL 122 configured to emit a beam of light 126 toward a target 130. As discussed with respect to FIG. 1A, the VCSEL 122 may emit the beam of light 126 under a forward current bias $I_{BIAS}$ 124 and may have a bias voltage supplied to the VCSEL 122. Further, reflections 132 may be reflected back toward the VCSEL 122 where a self-mixing interference operation may occur.

A photodetector 136 may be integrated with the VCSEL 122 and may be positioned beneath the VCSEL 122. As depicted, the VCSEL 122 and the photodetector 136 may be stacked on top of one another. In some embodiments, the VCSEL 122 may have one or more fixed or switchable linearly polarized outputs and the photodetector 136 may have one or more fixed or switchable linear polarizers.

The photodetector 136 may detect an operational change in the VCSEL 122 due to a self-mixing interference operation. For example, the VCSEL 122 may emit a portion of the laser light downwards into the photodetector 136 in addition to the transmitted beam of light 126. Any alterations in the light emitted by the VCSEL 122, such as alterations resulting from a self-mixing interference operation, may additionally be input to the photodetector 136. A current monitor 134 may measure a bias current $I_{PD}$ of the photodetector 136 which may be used to detect properties of the target 130.

Figure 1C:
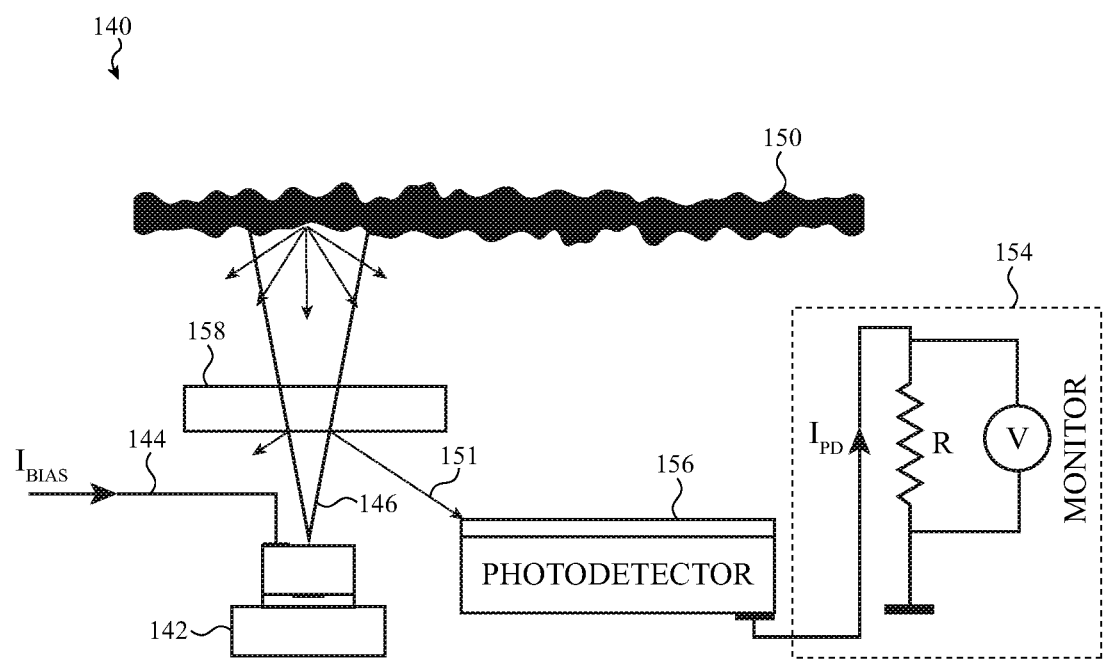
FIG. 1C depicts a VCSEL used to transmit a beam of light toward a target and an associated photodetector used to receive light reflected from the target, where the VCSEL and the photodetector are present at different locations.

FIG. 1C illustrates a self-mixing interferometry system 140 that uses a VCSEL 142 configured to emit a beam of light 146 toward a target 150. An intervening glass layer 158 may be provided to permit some reflections 151 to be directed toward an associated photodetector 156 before the beam of light 146 interacts with the target 150. The reflections 151 may be used by the photodetector 156 as an initial reference in detecting possible self-mixing interferometry operations. A current monitor 154 may measure a bias current $I_{PD}$ of the photodetector 156 which may be used to measure detected properties of the target 150. As discussed with respect to FIG. 1A, the VCSEL 142 may emit the beam of light 146 under a forward current bias $I_{BIAS}$ 144 and may have a bias voltage supplied to the VCSEL 142.

Though a VCSEL is described with respect to FIGS. 1A-1C, any type of light source may be used in accordance with the provided disclosure. In some embodiments, the VCSEL may be configured to perform a self-mixing interference operation only if the received light matches a polarity of the transmitted light. If the received light contains a mixture of light with various polarities, only the portion of light which shares a polarity of the transmitted light may be used in a self-mixing operation.

Figure 2A:
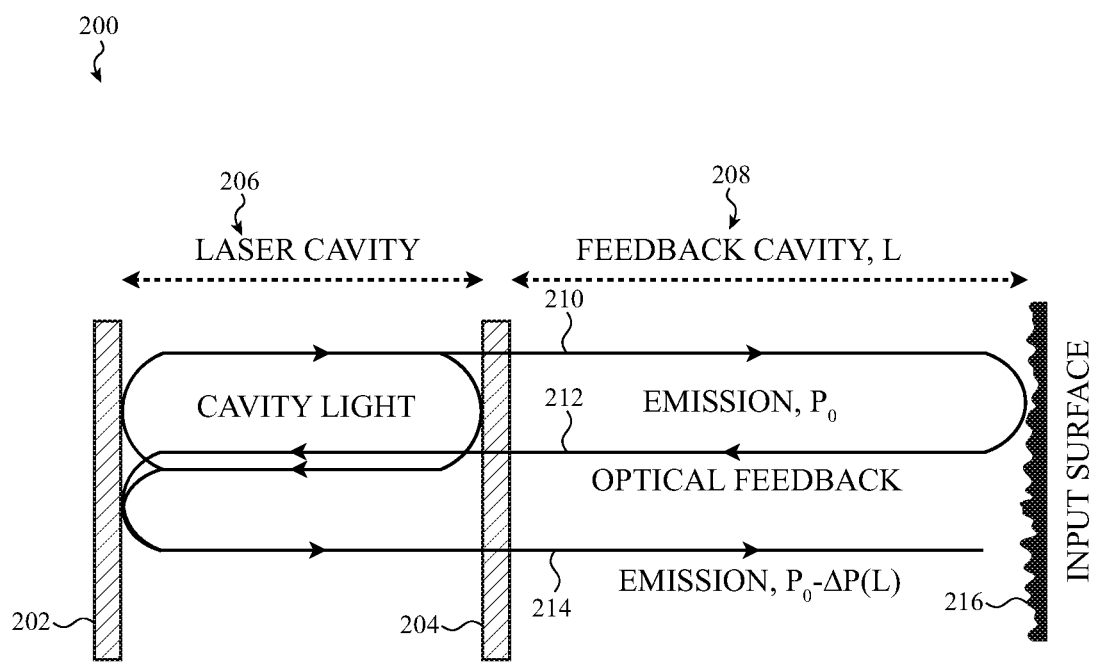
FIG. 2A depicts a diagram of a self-mixing interferometry operation.

FIG. 2A depicts a self-mixing interferometry operation 200 with respect to a light source (e.g., a VCSEL active area). The descriptions provided herein are intended only to describe certain aspects of self-mixing interferometry needed to understand the disclosed embodiments. Other aspects of self-mixing interferometry will be understood by one of ordinary skill in the art.

In FIG. 2A, the laser cavity 206 has a fixed length, which may be established at a time of manufacture and may be bounded by a mirror 202 and a partially-reflective mirror 204, and may emit a transmitted laser light 210 (e.g., an emission $P_0$) toward a target 216. The transmitted laser light 210 may travel through a feedback cavity 208 and to the target 216. The distance between the partially-reflective mirror 204 and the target 216 may be variable depending on the position of the laser cavity 206 with respect to the target 216. In the example depicted in FIG. 2A, the feedback cavity 208 has a length L.

Once the transmitted laser light 210 contacts the target 216, the laser light may be reflected as an optical feedback 212 back toward the laser cavity 206. The optical feedback 212 may pass through the partially-reflective mirror 204 and may re-enter the laser cavity 206 where a self-mixing interferometry process occurs. As the optical feedback 212 coherently interacts with the cavity light, a new transmitted combined laser light 214 may be created. The transmitted combined laser light 214 may have characteristics (e.g., a wavelength and/or power) that differ from the initial characteristics of the transmitted laser light 210. By performing certain analyses on the transmitted combined laser light 214 with respect to the transmitted laser light 210, detected properties of the target 216 with respect to the laser cavity 206 may be determined.

In some examples, the electromagnetic radiation/beams of light emitted by a self-mixing interferometry sensor may be generated by an electromagnetic radiation source such as a vertical-cavity surface-emitting laser (VCSEL); an edge-emitting laser; a vertical external-cavity surface-emitting laser (VECSEL); a quantum-dot laser (QDL); a quantum cascade laser (QCL); a light-emitting diode (LED) (e.g., an organic LED (OLED)); a resonant-cavity LED (RC-LED); a micro LED (mLED); a superluminescent LED (SLED); any solid state, fiber or other laser; and so on. The generated, emitted, and received electromagnetic radiation may include, for example, visible or invisible light (e.g., green light; infrared (IR) light; ultraviolet (UV) light; and so on). The output of a self-mixing interferometry sensor (i.e., the self-mixing interferometry signal) may include a photocurrent produced by a photodetector (e.g., a photodiode), which photodetector is integrated with, or positioned under, above, or next to, the sensor's electromagnetic radiation source. Alternatively or additionally, the output of a self-mixing interferometry sensor may include a measurement of the current or junction voltage of the self-mixing interferometry sensor's electromagnetic radiation source.

Figure 2B:
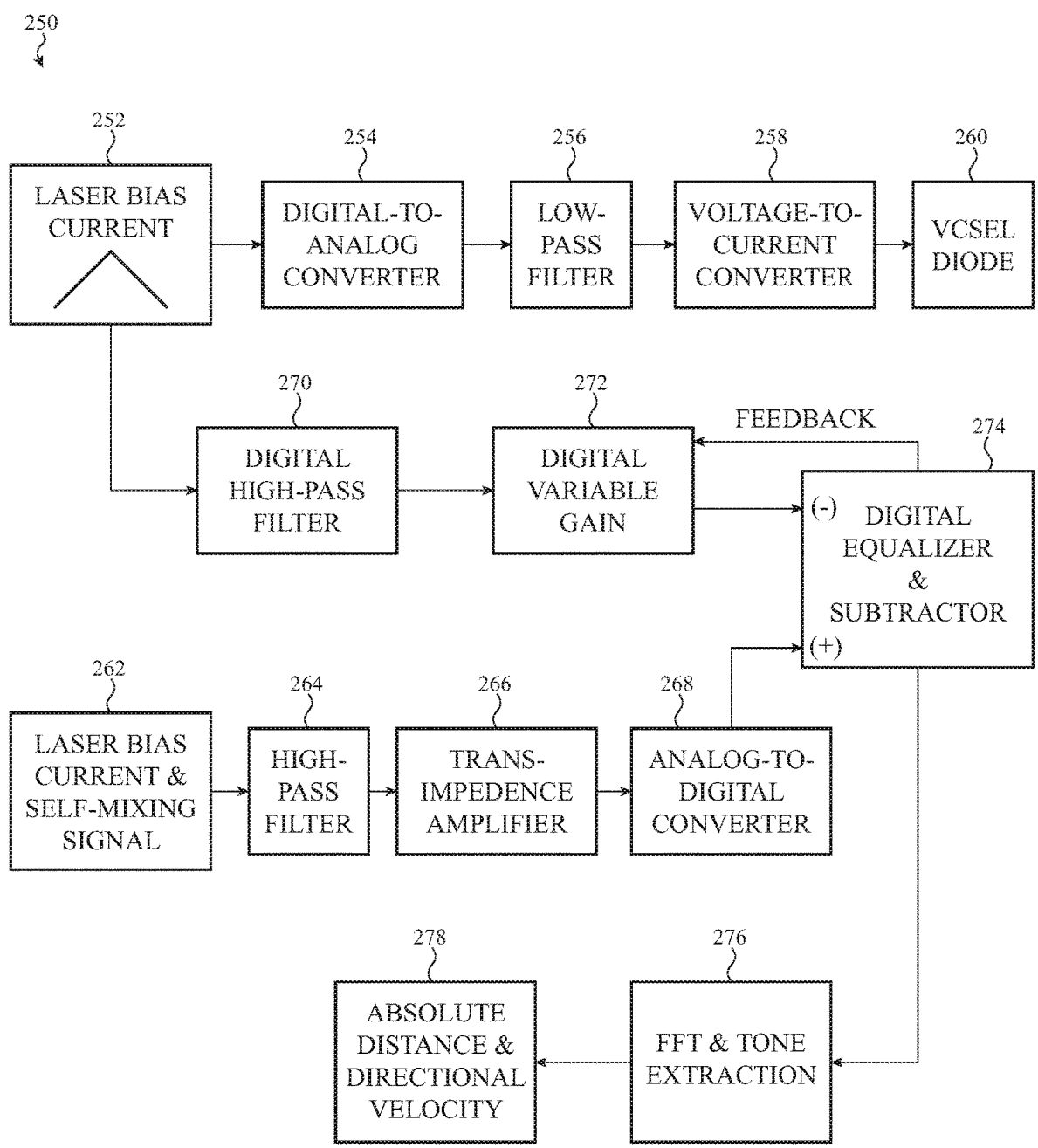
FIG. 2B depicts a block diagram of a circuit operable to implement analyses for determining inputs using self-mixing interferometry.

FIG. 2B depicts a block diagram of a system 250 that may implement a self-mixing interferometry operation and associated analyses. The system 250 may generate an initial digital signal and may process the digital signal to produce a triangle-modulated laser bias current 252 as an input to a bias current of a VCSEL 260. In an illustrated example, an initial step signal may be produced by a digital generator to approximate a triangle function (e.g., the triangle-modulated laser bias current 252). The triangle-modulated laser bias current 252 may be used as an input to a digital-to-analog (DAC) converter 254. The resulting voltage signal may then be filtered by a low-pass filter 256 to remove quantization noise. Alternatively, an analog signal generator may be used to generate an equivalent triangle voltage signal directly. The filtered voltage signal may then be input to a voltage-to-current converter 258 to produce the desired triangle-modulated laser bias current 252 in a form for input to the VCSEL 260.

As described above, reflections from a target may cause a self-mixing interferometry operation in the VCSEL 260 that results in an altered operational parameter of the VCSEL 260. This alteration may be measured or inferred, either from an operational parameter of the VCSEL 260 or from an operational parameter of an associated photodetector. These alterations may be measured to produce a signal 262 (e.g., a combination of the triangle-modulated laser bias current 252 and a self-mixing signal). The signal 262 may have been measured by a photodetector and may be a triangle wave combined with a smaller and higher frequency signal related to the changes in the interferometric parameter.

The signal 262 may be passed through a high-pass filter 264, which may convert the major ascending and descending ramp components of the signal 262 to DC offsets. As the signal 262 may be a current signal from a photodetector, a trans-impedance amplifier 266 may produce a corresponding voltage output for further processing.

The voltage output may then be sampled and quantized by an analog-to-digital converter (ADC) 268. Before immediately applying a digital fast Fourier transform (FFT) to the output of the ADC 268, an equalization may be applied in order to clear remaining residue of the triangle signal received by the photodiode, thus isolating the interferometric signal. The initial digital signal values from the digital generator used to produce the triangle modulated laser bias current 252 may be used as an input to a digital high-pass filter 270 to produce a digital signal to correspond to the output of the ADC 268. An adjustable gain may be applied by a digital variable gain circuit 272 to the output of the digital high-pass filter 270.

The output of the digital variable gain circuit 272 may be used as one input to the digital equalizer and subtractor 274. The other input to the digital equalizer and subtractor 274 may be the output of the ADC 268. The two signals may be differenced and may be used as part of a feedback to adjust a gain provided by the digital variable gain circuit 272.

Once a sufficient correlation is obtained by the feedback, an FFT and tone extraction circuit 276 may apply an FFT to the output of the digital equalizer and subtractor circuit 274. From the FFT spectra obtained, a property of the target (e.g., an absolute distance and directional velocity) may be inferred as indicated by block 278. During the FFT and tone extraction circuit 276 step, processing electronics associated with the self-mixing interferometry operation 200 may perform a frequency domain analysis on the signal received from the digital equalizer and subtractor 274. The frequency domain analysis may isolate signals corresponding to a change in an operational parameter of the VCSEL 260 and may be used to measure real-world events (e.g., a gesture, a distance between a target and a VCSEL, a speed of the target or the VCSEL, and so on).

The system 250 depicted in FIG. 2B is just one example of a potential system that implements a self-mixing interferometry operation and performs associated analyses. In additional or alternative embodiments, additional, fewer, or alternate circuits, converters, filters, currents, diodes, and so on, may be provided. For example, the laser bias current 252 provided as an input to a bias current of a VCSEL 260 is described above as a triangle-modulated current. In some embodiments, a laser bias current may be provided in a different waveform such as, for example, a sinusoidal, square, or sawtooth waveform, and so on. In this way, a VCSEL 260 may be driven by any number of waveforms and/or laser bias currents. As another example, a self-mixing signal may be analyzed in a way different than that shown in FIG. 2B. For example, a self-mixing signal may be interrogated and analyzed in a time domain. The above examples are merely provided as exemplary systems and any method or system for processing and/or analyzing self-mixing signals may be used in accordance with the provided disclosure.

Figure 3A:
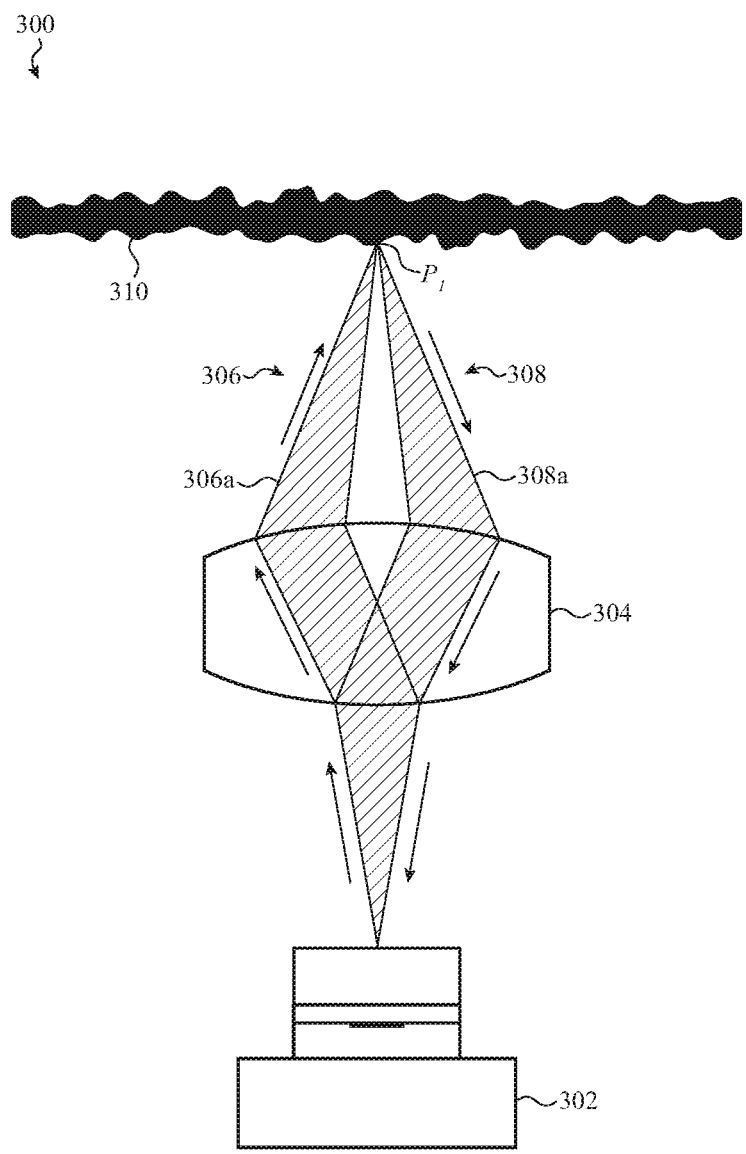
FIG. 3A depicts a self-mixing interferometry sensor and non-reciprocal paths for a transmitted beam of light and a received beam of light.

FIG. 3A may include the same kind of self-mixing interferometry sensors discussed with respect to FIGS. 1A-2B as discussed above. FIG. 3A depicts a self-mixing interferometry system 300 where a self-mixing interferometry sensor 302 transmits a transmitted laser light 306 along an illumination path 306a and receives a received laser light 308 from a collection path 308a. The illumination path 306a and the collection path 308a may have non-reciprocal portions, as depicted in FIG. 3A.

The non-reciprocal illumination path 306a and collection path 308a may be created by a set of one or more optical components, such as an optical circulator, birefringent optics, a birefringent optical circulator, and so on. As discussed herein, any type or collection of appropriate optics may be used to create a non-reciprocal path. In the depicted embodiment, birefringent optics 304 (e.g., a birefringent circulator) may be used to create non-reciprocal paths. In some examples, the illumination path 306a may end at the same location where the collection path 308a begins (e.g., the self-mixing interferometry system 300 is confocal). As used herein, the birefringent optics 304 may be positioned over an aperture of the self-mixing interferometry sensor 302 and may be used to direct emitted or received light.

The birefringent optics 304 may be formed of a material, or combination of materials, with a refractive index that depends on the polarization and/or propagation direction of light. In the example depicted in FIG. 3A, the birefringent optics 304 may have a first refractive index in the direction of travel of the transmitted laser light 306 and a second refractive index in the direction of travel of the received laser light 308. As used herein, the direction of travel of the transmitted laser light 306 may be referred to as a first direction of travel and the direction of travel of the received laser light 308 may be referred to as a second direction of travel. In this way, the paths (e.g., the illumination path 306a and the collection path 308a) may differ for transmitted and received laser light. The birefringent optics 304 are described in more detail with respect to, for example, FIGS. 4A-6C. In some embodiments, the birefringent optics 304 may be referred to as a birefringent circulator and/or a birefringent lens. In some embodiments, the birefringent optics 304 may include various lenses to collimate or otherwise focus received or transmitted light.

In some embodiments, the birefringent optics 304 may be configured to positive optical power as a finite conjugated optical system with a first aperture on a side closest to a self-mixing interferometry sensor 302 and with a second aperture closest to the target 310.

The self-mixing interferometry sensor 302 may initially transmit a beam of laser light 306. Before reaching the birefringent optics 304, the transmitted laser light 306 may follow a substantially straight path. Once the transmitted laser light 306 is received by the birefringent optics 304, a first refractive index of the birefringent optics 304 (e.g., a refractive index in a first direction) may result in the refraction of the transmitted laser light 306 as the transmitted laser light 306 moves through the birefringent optics 304. In FIG. 3A, the illumination path 306a of the transmitted laser light 306 is depicted substantially linearly with various interspersed angles. This depiction is intended for graphical simplicity and any illumination path 306a of the transmitted laser light 306 is possible.

The transmitted laser light 306 may enter the birefringent optics 304 at a first receiving location on the birefringent optics 304 and may travel along a first optical path within the birefringent optics 304. The transmitted laser light 306 may then exit the birefringent optics 304 at a first emission location.

Once the transmitted laser light 306 exits the birefringent optics 304 (e.g., at a first aperture on the birefringent optics 304), the transmitted laser light 306 may be directed toward a point $P_1$ on a target 310. As such, the illumination path 306a of the laser light and the collection path 308a of the reflected laser light may converge (or be commonly focused) at point $P_1$. In some embodiments, the illumination path 306a and the collection path 308a may be focused at a common point that is behind or in front of the target 310 instead of a point $P_1$ positioned on the target. The point $P_1$ may be referred to as a common detection space and may be a location on, behind, or in front of the target 310. In some embodiments, the common detection space may be a sensing location.

The target 310 may be at least partially reflective and may reflect the transmitted laser light 306 toward a direction at an angle different than the angle of incidence of the transmitted laser light 306, so as to enter the birefringent optics 304 at a second aperture different than the first aperture. Surface features present on the target 310 (e.g., grooves or protrusions) may be irregularly spaced and/or may be presented at different angles. As such, the reflected light may be reflected in a direction away from the location where the transmitted laser light 306 exited the birefringent optics 304. Therefore, the transmitted laser light 306 may enter the birefringent optics 304 at a first angle different than a second angle of a received laser light 308 as the received laser light 308 enters the birefringent optics 304.

The reflected light may be referenced as returned laser light 308 and may travel along a collection path 308a. The returned laser light 308 may travel toward the birefringent optics 304 and may enter the birefringent optics 304 at an aperture (e.g., a second aperture) different than the aperture where the transmitted laser light 306 exited the birefringent optics 304 (e.g., a first aperture). However, due to the nature of the birefringent optics 304, a refractive index of the birefringent optics 304 along a direction of travel of the returned laser light 308 may be different than the refractive index in the opposite direction (e.g., as experienced by the transmitted laser light 306). Therefore, the birefringent optics 304 may guide the returned laser light 308 back toward the self-mixing interferometry sensor 302 and the received laser light 308 may undergo a self-mixing process when received by the self-mixing interferometry sensor 302, as discussed herein. In this way, partially or completely non-reciprocal paths may be used in a self-mixing operation.

The returned laser light 308 may enter the birefringent optics 304 at a second receiving location on the birefringent optics 304 and may travel along a second optical path within the birefringent optics 304. The transmitted laser light 306 may then exit the birefringent optics 304 at a second emission location. As depicted in FIG. 3A, the first optical path may be different from the second optical path.

Various applications may be used in accordance with the confocal example depicted in FIG. 3A.

For example, a surface roughness of the target 310 may be measured based on properties of the returned beam of light 308. The surface roughness of the target 310 may be determined, for example, when the roughness of the target (e.g., root mean squared (RMS) roughness) is higher than a one-half wavelength value, equal to a one-half wavelength value, or less than a one-half wavelength value by utilizing a self-mixing specklegram. As a speckle topography (e.g., a roughness of an input surface) may result in light reflecting at a number of different angles, a self-mixing interferometry sensor with circulator optics, as described herein, may be used to measure a surface roughness even when the roughness is higher than a half-wavelength of light. In this way, a speckle sensitivity range may be increased.

Figure 3B:
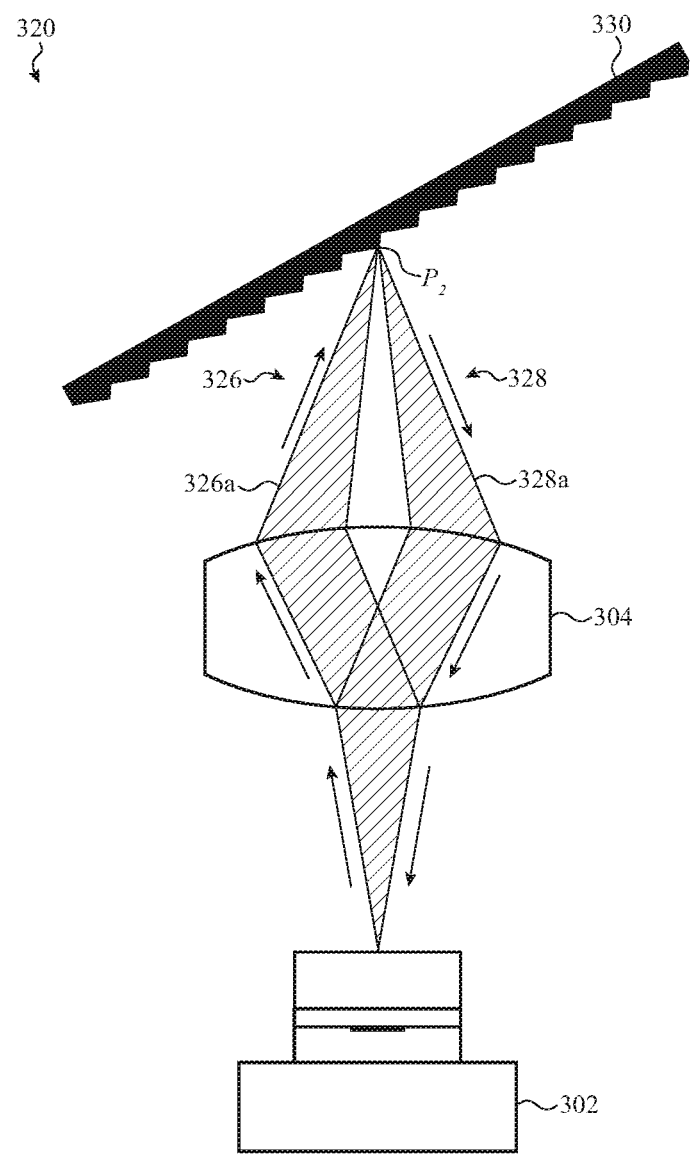
FIG. 3B depicts a self-mixing interferometry sensor and non-reciprocal paths for a transmitted beam of light and a received beam of light where the detected object is a periodic structure.

In alternative or additional examples, a target may be a two-dimensional or three-dimensional periodic structure such as, for example, a diffractive grating. The system 320 depicted in FIG. 3B illustrates an example of such an arrangement. The system 320 includes a self-mixing interferometry sensor 302 and birefringent optics 304 as discussed with reference to FIG. 3A. Likewise, the system 320 may include transmitted laser light 326 following an illumination path 326a and returned laser light 328 following a collection path 328a. Aspects of the transmitted laser light 326 and the returned laser light 328 may be similar to the respective transmitted laser light and returned laser light discussed above.

A target 330 may have a periodic structure, as depicted. Such a periodic structure may have repeating features such as ridges, protrusions, and/or valleys. To measure certain detected properties of such a periodic structure, an angular difference between an illumination path 326a and a collection path 328a may be selected in accordance with repeating features of the periodic structure (e.g., a diffraction order of a diffractive grating). By selecting corresponding angular differences and periodic structures, non-reciprocal sensing paths may be used to obtain high fidelity self-mixing measurements of detected properties. In this way, a periodicity of the target may be measured.

The point $P_2$ at which the transmitted laser light 326 and the returned laser light 328 meet on the target 330 may be positioned at any location on the target 330. In some embodiments, the point $P_2$ may be positioned on a slope of the target 330 and an angle of the illumination path 326a and the collection path 328a may correspond to the slope of the target 330. In some embodiments, a location of the point $P_2$ may change as the target 330 moves relatively from the self-mixing interferometry sensor 302.

Figure 3C:
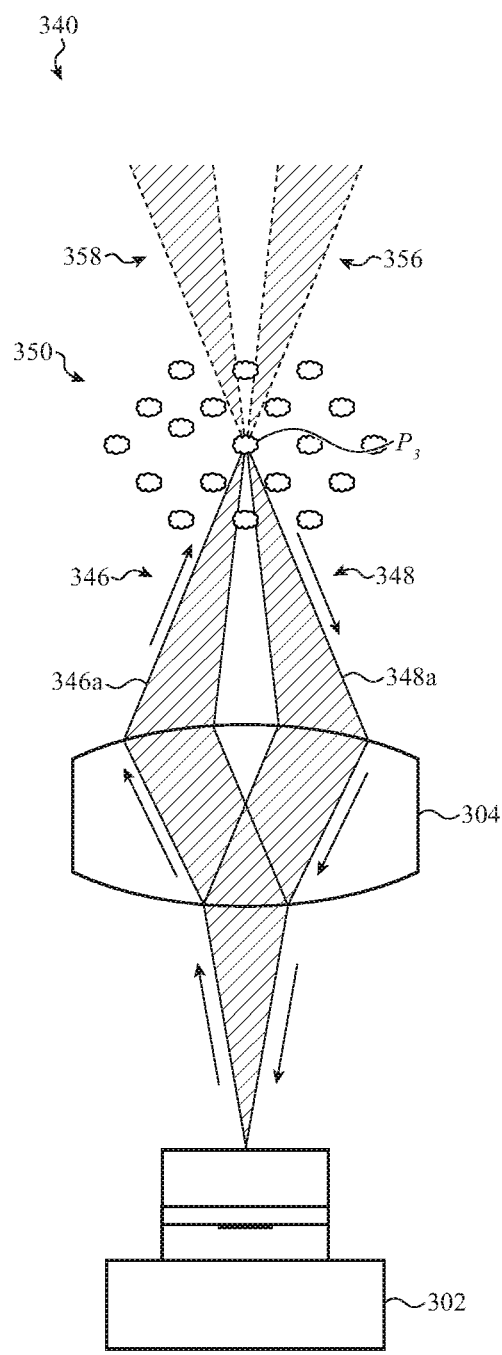
FIG. 3C depicts a self-mixing interferometry sensor and non-reciprocal paths for a transmitted beam of light and a received beam of light where the detected object is a number of particles.

In alternative or additional examples, a target, instead of being an object as depicted in FIGS. 3A and 3B, may be a number of particles (e.g., smoke particles, red blood cells, and so on). For example, FIG. 3C depicts a system 340 where a self-mixing interferometry sensor 302 and birefringent optics 304 operate to direct and receive non-reciprocal light paths toward a number of particles 350. The number of particles 350 may include any particle or collection of particles, either uniform particles or mixed particles, and may include, for example, cells; smoke particles; dust; water particles; and so on. The number of particles 350 may further have any number of densities; physical properties; concentration; and so on.

As discussed, the system 340 includes a self-mixing interferometry sensor 302 and birefringent optics 304 as discussed with reference to FIG. 3A. Likewise, the system 340 may include transmitted laser light 346 following an illumination path 346a and returned laser light 348 following a collection path 348a. Aspects of the transmitted laser light 346 and the returned laser light 348 may be similar to the respective transmitted laser light and returned laser light discussed above.

As the number of particles 350 may exist in a three-dimensional space, a first subset of the particles may exist at or pass through a point $P_3$ (e.g., a confocal point where the illumination path 346a and the collection path 348a meet) and a second subset of particles that do not exist at or pass through point $P_3$. The first subset of particles may be considered "in-focus particles" and the second subset of particles may be considered "out-of-focus particles." In self-mixing systems without non-reciprocal optics (e.g., systems completely overlapping illumination and collection paths), it may be difficult to differentiate between in-focus particles and out-of-focus particles as, for example, in-focus particles with a small size and low reflectivity may result in self-mixing signals similar to those produced from out-of-focus particles with a large size and high reflectivity. However, in the system depicted in FIG. 3C, since the illumination path 346a and the collection path 348a only overlap at point $P_3$ (e.g., the confocal point), in-focus particles (e.g., particles at and/or passing through point $P_3$) may be distinguishable from out-of-focus particles due to different directions and/or polarity of reflected light.

Light beams 356 and 358 depict the continuation of beams 346 and 348 in the event that beams 346 and 348 are not blocked by a particle of the number of particles 350. While a portion of light beams 358 and 356 may return to the birefringent optics 304 after interacting with any number of particles (e.g., out-of-focus particles), the signal generated in response to out-of-focus particles may be distinguishable from signals generated in response to in-focus particles, as described above.

Figure 3D:
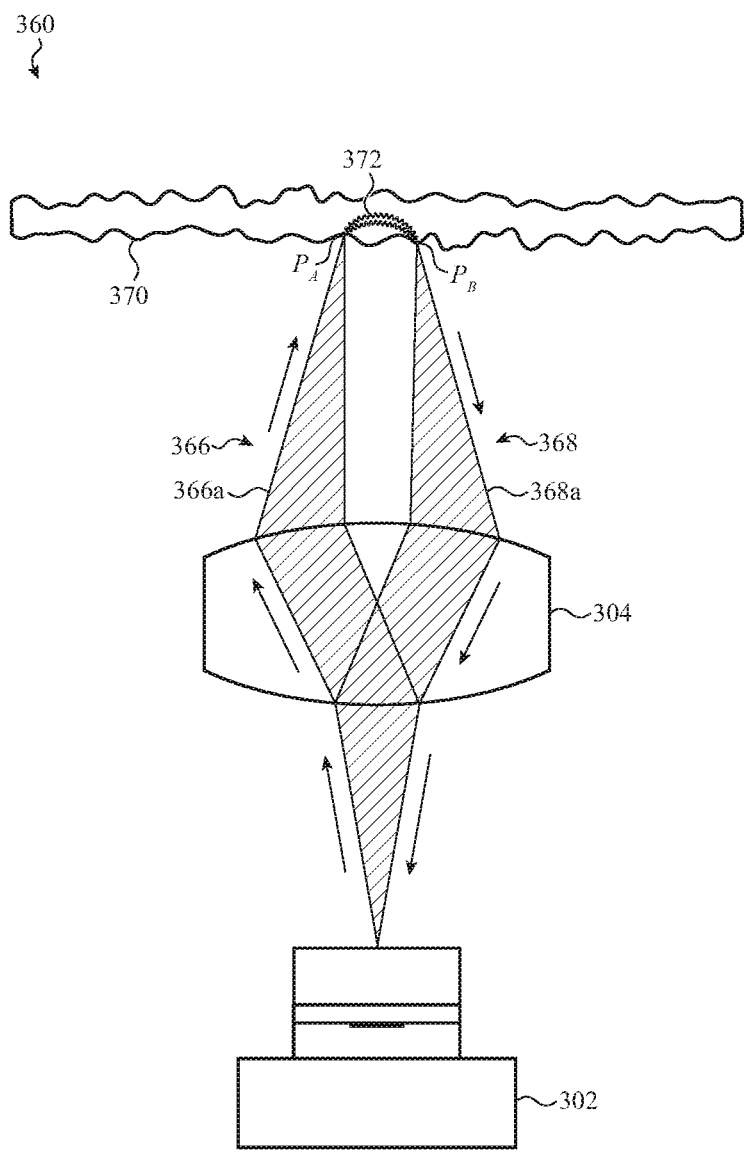
FIG. 3D depicts a self-mixing interferometry sensor, including non-reciprocal paths for a transmitted beam of light and a received beam of light, and including a first location where the transmitted beam of light contacts a target and a second location where the received beam of light returns from the target.

FIG. 3D may contain substantially similar structures as discussed with reference to FIGS. 3A-3C. Notably, FIG. 3D depicts a non-confocal arrangement, where the illumination path 366a and the collection path 368a impact an object at different points, a first point $P_A$ and a second point $P_B$. Light may travel through a curved path 372 underneath a surface of an object before being emitted from the object at a different location. FIG. 3D depicts a self-mixing interferometry system 360 where a target 370 may be partially transparent with respect to at least a portion of transmitted laser light 366 and may have a number sub-surface features below a surface of the target 370. For example, the target 370 may be a portion of a human body such as a layer of skin. Objects below the target 370 may include blood vessels, tissue, and so on. In this embodiment, transmitted laser light 366 may be transmitted from the self-mixing interferometry sensor 302, may be directed toward a point $P_A$ and returned laser light 368 may be reflected from a point $P_B$. The transmitted laser light 366 may follow an illumination path 366a, may reach point $P_A$, may travel within a portion underneath the target 370, along a curved path 372 (e.g., a "banana" path), and may exit the target 370 at point $P_B$. After leaving point $P_B$, returned laser light 368 may follow a collection path 368a and may return through the birefringent optics 304 to the self-mixing interferometry sensor 302. As used herein, $P_A$ may be referred to as a first location and $P_B$ may be referred to as a second location. In some embodiments, $P_A$ and $P_B$ may be underneath a surface of the target 370, in front of the target 370, or may be positioned along the target 370. As used herein, the birefringent optics 304 may be positioned over an aperture of the self-mixing interferometry sensor 302 and may be used to direct emitted or received light.

In the self-mixing interferometry system 360, a property of sub-surface features underneath the target 370 may be measured. For example, a displacement or movement of blood flowing through veins may be measured by self-mixing interferometry operations so that, for example, a user's heart rate; blood oxygenation level; blood pressure; and so on may be determined. In some examples, a user's body mass index (BMI) may be measured by modelling reflective/absorption properties of different kinds of cells (e.g., fat cells or muscle cells). In alternate or additional examples, bone and/or muscle movement may be detected by a self-mixing interferometry system, such as described herein, and may be used to determine a gesture of a user's hand, wrist, arm, and so on. In this way, signal saturation from surface reflection off of a user's skin may be eliminated or reduced.

In some embodiments, the self-mixing interferometry system 360 may measure a Doppler frequency shift beneath the target 370 (e.g., with blood or tissue beneath a user's skin). As the light travels along the curved path 372, a property of the light may change. This changing property may be a changing frequency of light thereby resulting in a Doppler frequency shift. The returning light may carry this Doppler shift and the self-mixing interferometry sensor 302 may perform self-mixing analyses to measure sub-dermal measurements such as a blood flow rate (e.g., a blood flowmetry) By this arrangement, any fluid may be measured (e.g., a flowmetry of any fluid may be measured). For example, a water flow, a stomach acid flow, and the like may be measured either as a sub-dermal feature or as a surface measurement.

As an additional or alternative embodiment, a photoplethysmogram (PPG) may be measured as a sub-dermal measurement. A PPG may refer to an optically obtained plethysmogram that detects a blood volume change with a bed of tissue. By detecting blood volume changes, information about a user's cardiovascular system may be obtained. The PPG measurement may be obtained directly from blood volume or may be inferred from related features (e.g., skin)

that absorbs and/or reflects different amounts of light depending on an amount of blood volume.

Figure 3E:
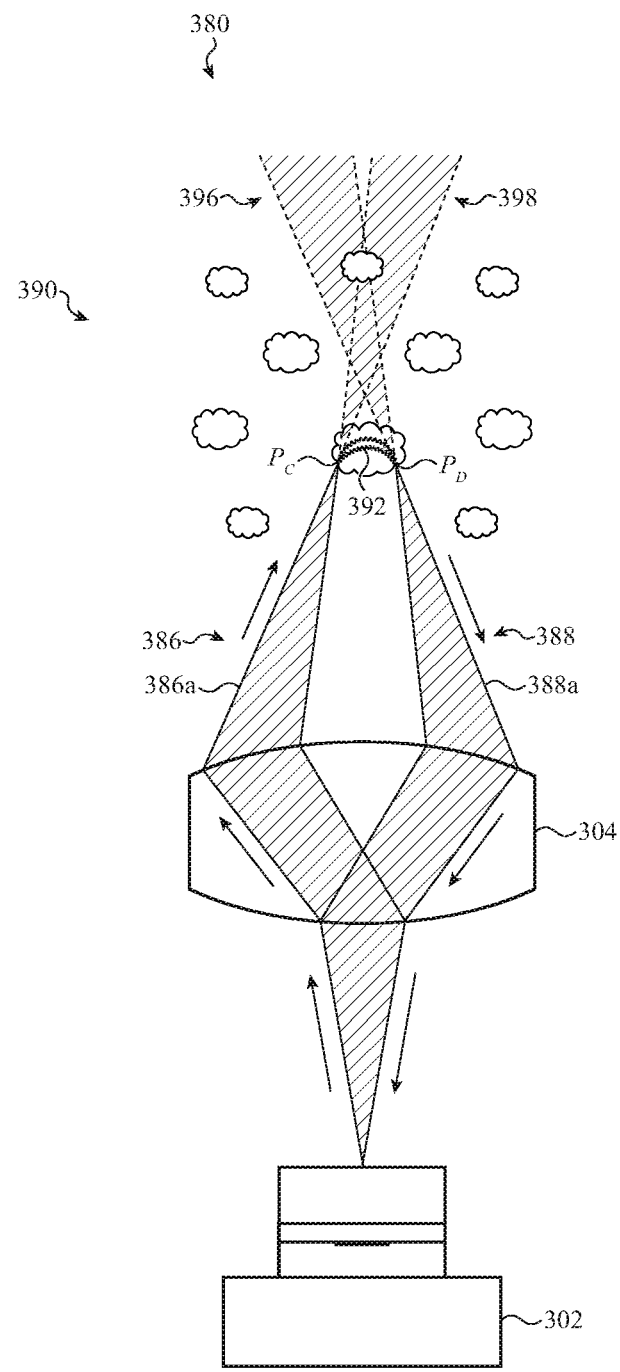
FIG. 3E depicts a non-confocal sensing system including a self-mixing interferometry sensor and non-reciprocal paths for a transmitted beam of light and a received beam of light where the detected object is one of a number of particles.

FIG. 3E depicts a system 380 for an additional non-confocal arrangement where transmitted laser light 386 impacts a particle from a number of particles 390 at a first point $P_c$ and received laser light 388 is emitted from the particle at a second point $P_D$. The system 380 may include a self-mixing interferometry sensor 302, birefringent optics 304, transmitted laser light 386 following an illumination path 386a, and received laser light 388 following a collection path 388a.

As discussed in the non-confocal system of FIG. 3D, a curved path 392 extending through an object may connect the illumination path 386a and the collection path 388a. In the depicted example, the object may be a particle from a number of particles 390 and the curved path 392 may extend through a diameter of the particle. Based on a changing property of light as it travels through the curved path 392, as discussed above, a property of the particle may be measured through self-mixing operations. For example, a diameter of the particle may be determined based on differences between the transmitted laser light 386 and the received laser light 388 as measured by the self-mixing interferometry sensor 302.

Light beams 396 and 398 depict the continuation of beams 386 and 388 in the event that beams 386 and 388 are not blocked by a particle of the number of particles 390. While a portion of light beams 396 and 398 may return to the birefringent optics 304 after interacting with any number of particles, the signal generated in response to out-of-focus particles may be distinguishable from signals generated in response to non-confocal detection, as described above.

Figure 4A:
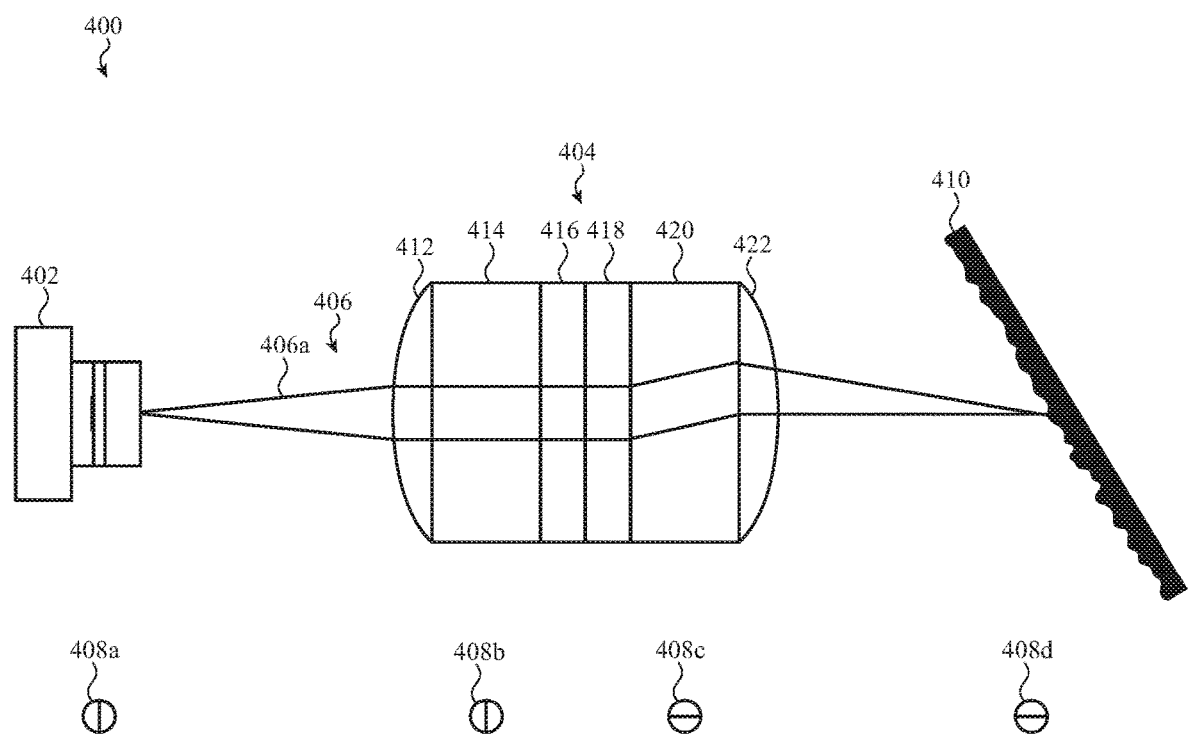
FIG. 4A depicts a beam of light with a vertical polarity transmit from a self-mixing interferometry sensor, through a birefringent circulator, and toward a target.

FIG. 4A depicts a transmitted beam of light 406 emitted from a self-mixing interferometry sensor 402 with a vertical polarization 408a (e.g., a p-polarization). As used herein, the polarization 408a may be referenced as a first polarization. Though the initial polarity is described as a vertical polarization, any kind of polarization at any angle may be used in accordance with this disclosure. The self-mixing interferometry sensor 402 may be the same self-mixing interferometry sensors as discussed with reference to FIGS. 1A-3B and the birefringent circulator 404 may likewise be the same type of optics as birefringent optics 304, with respect to FIGS. 3A and 3B. As used herein, the birefringent optics 404 may be positioned over an aperture of the self-mixing interferometry sensor 402 and may be used to direct emitted or received light.

In FIG. 4A, the transmitted beam of light 406 may move through the birefringent circulator 404. The birefringent circulator 404 may include a first lens 412, a first birefringent material 414, a Faraday rotator 416, a half-wave plate 418, a second birefringent material 420, and a second lens 422. The included optics are merely exemplary and any optics or combination of optics may be used in accordance with the present disclosure.

The first lens 412 may collimate the transmitted beam of light 406 so that the beam length of the transmitted beam of light 406 is relatively consistent throughout the birefringent circulator 404. The first lens 412 may also serve to focus a collimated beam toward the self-mixing interferometry sensor 402 when a beam of light travels in the opposite direction (see, e.g., FIG. 4B). The second lens 422 may focus a collimated beam to a particular point. In addition, the second lens 422 may collimate a beam when a beam is reflected off of a target 410. The first lens 412 and the second lens 422 may be referred to as collimating lenses or merely lenses. Any suitable lens may be used for the first lens 412 and the second lens 422 such as, but not limited to, geometric and/or refractive lenses fabricated from bulk; flat optics (e.g., diffractive and meta-surface flat optics); and so on.

The first birefringent material 414 may be bonded, or otherwise in proximity, to the first lens 412 and may refract components of the transmitted beam of light 406. As understood by one of ordinary skill in the art, birefringent materials may have different refractive properties depending on a polarization and/or propagation direction of light resulting in ordinary rays (o-rays) or extraordinary rays (e-rays). As such, the first birefringent material 414 may refract the transmitted beam of light 406 differently based on a polarization of the transmitted beam of light 406. Additionally, a returned beam of light may be refracted differently than the transmitted beam of light 406, such as discussed herein. Any material or combination of materials with birefringent properties may be used as the first birefringent material 414 and the second birefringent material 420. The first birefringent material 414 and the second birefringent material 420 may be fabricated from bulk; liquid crystals; meta-surfaces or meta-structures; and so on.

A Faraday rotator 416 may be bonded, or otherwise in proximity, to the first birefringent material 414. Though described as a Faraday rotator, any manner of rotator may be used in accordance with the disclosure. The Faraday rotator 416 may be a polarization rotator and may change a polarization of the transmitted beam of light 406 as the transmitted beam of light 406 moves through the Faraday rotator 416. The Faraday rotator 416 may use a magnet (e.g., a permanent magnet) and/or electromagnetic mechanisms to affect a polarization of the transmitted beam of light 406. The angle of polarization rotation may be calculated by the equation $\beta=VBd$, where $\beta$ is the angle of rotation, V is the Verdet constant for the material of the Faraday rotator 416, B is the magnetic flux density in the direction of propagation, and d is the length of the Faraday rotator 416.

The Faraday rotator 416 may be a non-reciprocal optical element. For example, a beam of light transmit in one direction through the Faraday rotator 416 may be initially rotated 20 degrees clockwise. If the rotated beam is reflected and re-enters the Faraday rotator 416 from an opposite direction, the initial rotation may not be canceled (e.g., the beam of light is not rotated 20 degrees counter-clockwise) but may be doubled (e.g., the beam of light is additionally rotated 20 degrees clockwise, such that the complete rotation of the beam of light is 40 degrees clockwise with respect to the transmitted beam of light). This property will be discussed in further detail with respect to FIGS. 6A and 6B.

A half-wave plate 418 may be bonded, or otherwise in proximity, to the Faraday rotator 416. The half-wave plate 418 may be any type of wave plate and may affect a polarization of the transmitted beam of light 406. For example, the half-wave plate 418 may have a fast axis of 67.5 degrees, and any fast axis or other optical property may be used in accordance with the provided disclosure. Additionally, other types of wave plates may be used including, but not limited to, a quarter-wave plate or a full-wave plate. Unlike the Faraday rotator 416, the half-wave plate may be reciprocal and may cancel or revert an applied polarization when a beam of light returns through another side of the half-wave plate 418. In some embodiments, the half-wave plate may have an optical axis between 60 degrees and 75 degrees and/or aligned to a polarization of the transmitted beam of light 406. In some embodiments, the half-wave plate may have any possible optical axis or other optical property.

The second birefringent material 420 may be formed of the same material or combination of materials as the first birefringent material 414 or may be formed of another material or combination of materials. The second birefringent material 420 may direct the transmitted beam of light 406 along a particular illumination path 406a depending on a polarity of the transmitted beam of light 406. A second lens 422 may additionally be provided to focus the transmitted beam of light 406 onto a target 410.

A polarization change of the transmitted beam of light 406 as the transmitted beam of light 406 travels along the illumination path 406a will now be described in accordance with the self-mixing interferometry system 400. When the transmitted beam of light 406 is initially emitted from the self-mixing interferometry sensor 402, the transmitted beam of light 406 may have a p-polarization 408a. This p-polarization 408a may remain consistent (e.g., as p-polarization 408b) as the transmitted beam of light 406 travels through the first birefringent material 414 in one propagation direction and when the p-polarization 408a is aligned with an ordinary axis of the first birefringent material 414. That is, an ordinary ray of the transmitted beam of light 406 may travel through the first birefringent material 414, without refraction, as the p-polarization 408a is aligned with the ordinary axis of the first birefringent material 414. The Faraday rotator 416 and the half-wave plate 418 may act in combination to change the p-polarization 408b into an s-polarization 408c. This s-polarization 408c may remain consistent and may come into contact with the target as s-polarization 408d. The illumination path 406a may be altered from the path of the transmitted beam of light 406 through the first birefringent material 414 when the s-polarization 408c is aligned with an extraordinary axis of the second birefringent material 420. That is, an extraordinary ray of the transmitted beam of light 406 may travel through the second birefringent material 420, as refracted, as the s-polarization 408c is aligned with the extraordinary axis of the second birefringent material 420. Described simply and with reference to FIG. 4A, an ordinary ray component of the transmitted beam of light 406 is depicted as traveling through the first birefringent component 414 and an extraordinary ray component of the transmitted beam of light 406 is depicted as traveling through the second birefringent component 420. As used herein, the polarization 408d may be referred to as a second polarization.

Figure 4B:
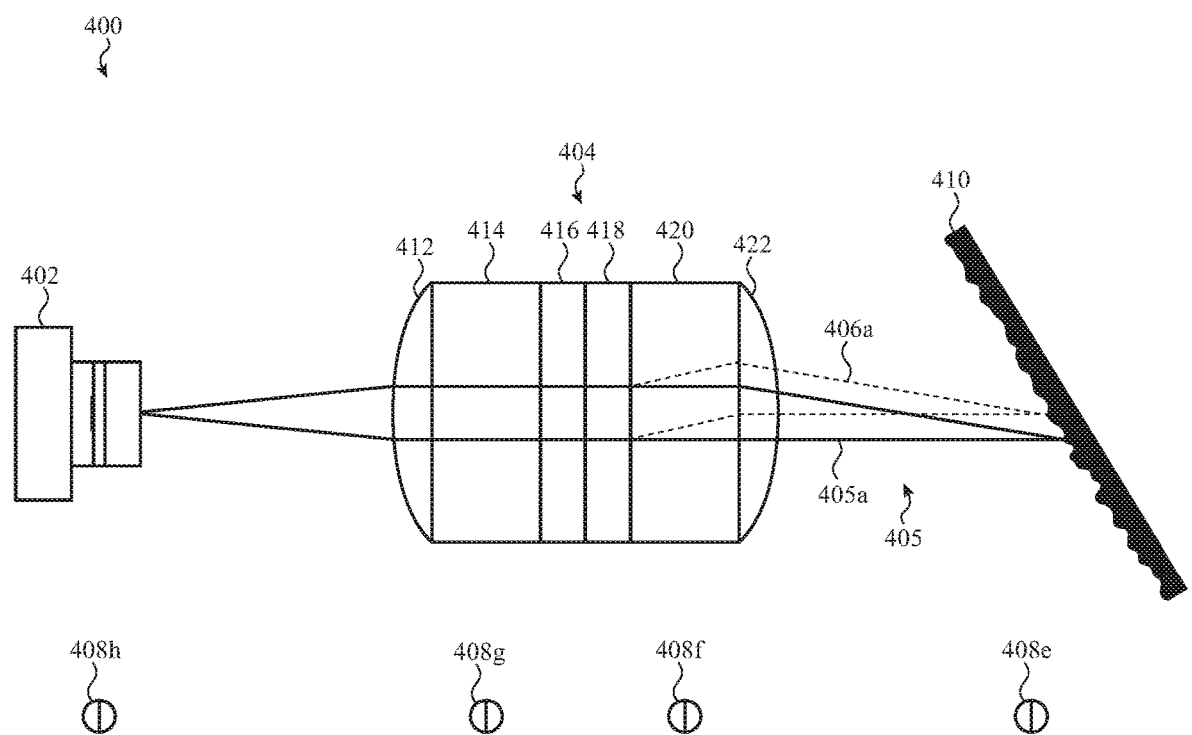
FIG. 4B depicts a beam of light reflected from a target, through a birefringent circulator, and toward a self-mixing interferometry sensor, where the received beam of light has the same polarity as the polarity transmit from the self-mixing interferometry sensor in FIG. 4A.

FIG. 4B depicts the self-mixing interferometry system 400, as described with respect to FIG. 4A, at an instance after the transmitted beam of light reflects off of the target 410 and returns to the self-mixing interferometry sensor 402 as a returned beam of light 405. The returned beam of light 405 may travel along a collection path 405a. The illumination path 406a as described with respect to FIG. 4A is depicted in phantom to facilitate a comparison between the illumination path 406a and the collection path 405a. Identically numbered components present in FIG. 4B are identical to those described herein.

Figure 4C:
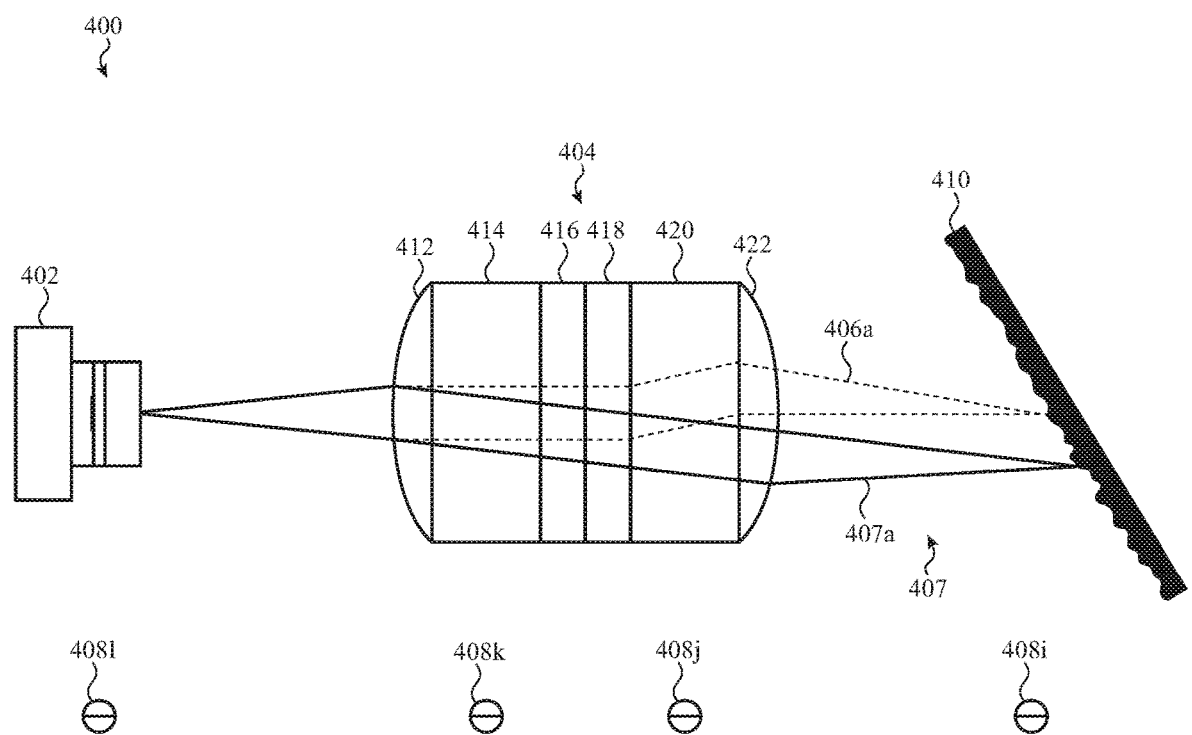
FIG. 4C depicts a beam of light reflected from a target, through a birefringent circulator, and toward a self-mixing interferometry sensor, where the received beam of light has a polarity different from the polarity transmit from the self-mixing interferometry sensor in FIG. 4A.

Once the transmitted beam of light 406 reflects from the target 410, the returned beam of light may comprise light with multiple polarization states (e.g., s-polarization and p-polarization states) from single and multi-pass reflection and light scattering at or below a surface of the target 410. FIG. 4B depicts the component of the returned beam of light 405 with p-polarization 408e and FIG. 4C depicts the component of the returned beam of light 407 with s-polarization 408i.

In FIG. 4B, the returned beam of light 405 reflects from the target 410 with a p-polarization 408e. As the returned beam of light 405 moves along the collection path 405a, the polarization stays as p-polarization as it moves through the second birefringent material 420 (e.g., p-polarization 408f), the first birefringent material 414 (e.g., p-polarization 408g), and as it is received by the self-mixing interferometry sensor 402 (e.g., p-polarization 408h). Though the returned beam of light 405 has a p-polarization along each of these markers, the returned beam of light 405 does not necessarily remain at a p-polarization throughout the entirety of the collection path 405a. The half-wave plate 418 may shift the polarization of the returned beam of light 405 to a certain degree, though this shift may be canceled by the Faraday rotator 416 (see, e.g., FIGS. 6A and 6B). As depicted in FIG. 4B, an ordinary ray component of the returned beam of light 405 does not refract as it moves through the first birefringent material 414 and the second birefringent material 420 as the ordinary ray component is aligned with the ordinary axes of each of the first birefringent material 414 and the second birefringent material 420.

In some embodiments, a portion of the collection path 405a between the self-mixing interferometry sensor 402 and the first lens 412 may fully overlap with a portion of the illumination path 406a between the self-mixing interferometry sensor 402 and the first lens 412. In this way, the returned beam of light 405 may return to the self-mixing interferometry sensor 402 with coherent mode/polarization matching with respect to the transmitted beam of light 406.

Both the p-polarization 408f and the p-polarization 408g may align with the ordinary axis of both the first birefringent material 414 and the second birefringent material 420. There may therefore be a region at or below a surface of the target 410 where the returned beam of light 406 travels along the collection path 405a. This region at or below the surface of the target 410 may be a region of interest and may be a region where properties of or associated with the target 410 are detected.

In FIG. 4C, the returned beam of light 407 reflects from the target 410 with an s-polarization 408i. As the returned beam of light 407 moves along the collection path 407a, the polarization stays as s-polarization as it moves through the second birefringent material 420 (e.g., s-polarization 408j), the first birefringent material 414 (e.g., s-polarization 408k), and as it is received by the self-mixing interferometry sensor 402 (e.g., s-polarization 408l). Though the returned beam of light 407 has an s-polarization along each of these markers, the returned beam of light 407 does not necessarily remain at an s-polarization throughout the entirety of the collection path 407a. The half-wave plate 418 may shift the polarization of the returned beam of light 407 to a certain degree, though this shift may be canceled by the Faraday rotator 416 (see, e.g., FIGS. 6A and 6B).

As depicted in FIG. 4C, an extraordinary ray component of the returned beam of light 407 refracts as it moves through the first birefringent material 414 and the second birefringent material 420 as the extraordinary ray component is not aligned with the ordinary axes of each of the first birefringent material 414 and the second birefringent material 420. The extraordinary ray component of the returned beam of light 407, therefore, may move through both the first birefringent material 414 and the second birefringent material 420 as depicted in FIG. 4C.

Here, it is noted that the self-mixing interferometry sensor 402 may, in some embodiments, only be able to perform self-mixing processes if the polarization of the returned light matches the polarization of the transmitted laser light. In this case, the s-polarized light depicted in FIG. 4C may enter the self-mixing interferometry sensor 402 but may not affect any self-mixing interference process (since light with p-polarization was initially transmit). In additional or alternative embodiments, the s-polarized light may be prevented from entering the self-mixing interferometry sensor 402 by, for example, a linear p-polarizer integrated to the self-mixing interferometry sensor. In some embodiments, different birefringent circulators may be used such that received light has the same polarization as the transmitted light in every circumstance. For example, a polarization insensitive optical circulator may be used, as understood by a person of ordinary skill in the art. The polarization 408*i* may be referred to as a third polarization and the polarization 408*l* may be referred to as a fourth polarization.

The difference between the illumination path 406*a*, the collection path 405*a*, and the collection path 407*a* may depend on polarization values of light traveling on the paths and a direction of propagation of the light through the birefringent circulator. For example, p-polarization may interact with an ordinary axis of birefringent elements to travel along a certain path. Similarly, s-polarization may interact with an extraordinary axis of birefringent elements to travel along another, at least partially distinct, path. Due to the birefringent properties discussed herein, non-reciprocal optics may be formed. Ordinary ray components and extraordinary ray components may move through each of the birefringent elements depending on whether the ray is aligned with an ordinary axis or an extraordinary axis of the birefringent elements.

Though the illumination and collection paths are depicted with certain boundaries, it is noted that these boundaries are for graphical purposes only. Any illumination or collection path from or to a light source, through a birefringent circulator, and to or from a target may be used in accordance with the present disclosure.

Figure 5A:
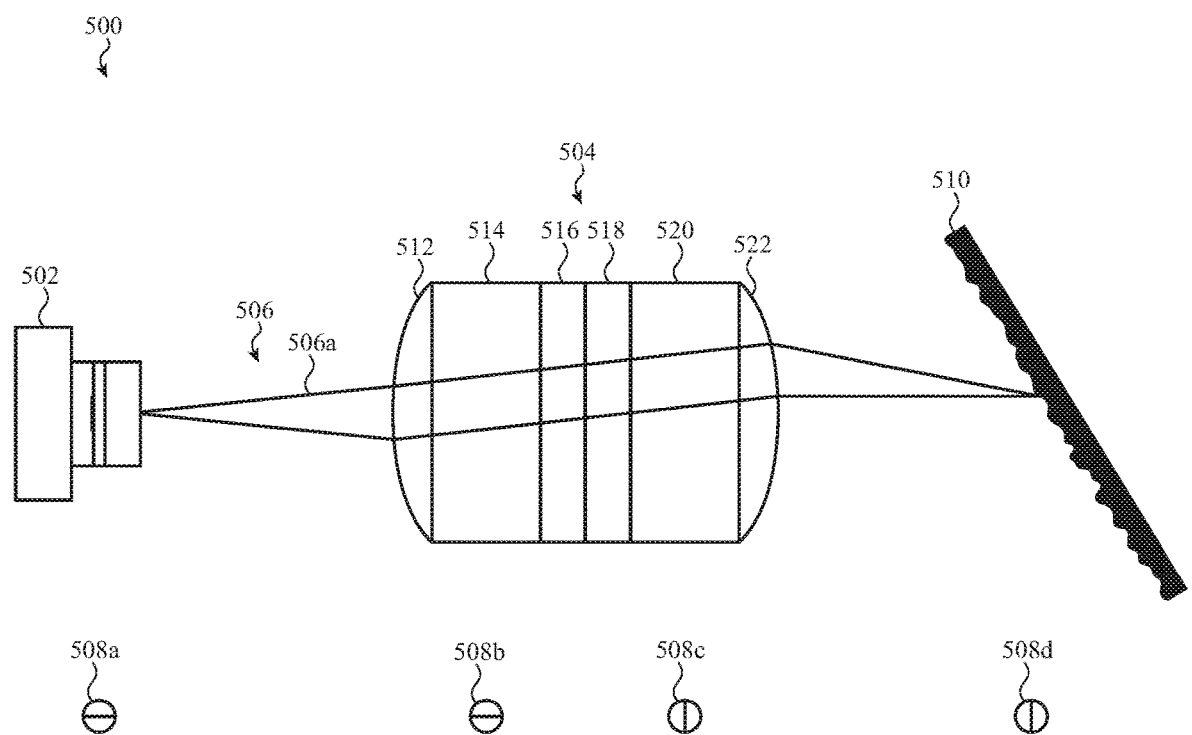
FIG. 5A depicts a beam of light with a horizontal polarity transmit from a self-mixing interferometry sensor, through a birefringent circulator, and toward a target.

FIG. 5A depicts a transmitted beam of light 506 emitted from a self-mixing interferometry sensor 502 with a horizontal polarization (e.g., an s-polarization). Similar reference numbers in FIGS. 5A-5C may correspond to their counterparts in FIGS. 4A-4C and the structures depicted in FIGS. 5A-5C may be substantially similar to those depicted in FIGS. 4A-4C. In some embodiments, the self-mixing interferometry system 500 may include substantially similar components as the self-mixing interferometry system 400.

In FIG. 5A, the transmitted beam of light 506 may move through the birefringent circulator 504. The birefringent circulator 504 may include a first lens 512, a first birefringent material 514, a Faraday rotator 516, a half-wave plate 518, a second birefringent material 520, and a second lens 522. The included optics are merely exemplary and any optics or combination of optics may be used in accordance with the present disclosure to produce non-reciprocal light paths.

The first lens 512 may collimate the transmitted beam of light 506 so that the beam length of the transmitted beam of light 506 is relatively consistent throughout the birefringent circulator 504. The first lens 512 may also serve to focus a collimated beam toward the self-mixing interferometry sensor 502 when traveling in the opposite direction. The second lens 522 may focus a collimated beam to a particular point on the target 510. In addition, the second lens 522 may collimate a beam when the beam is reflected off of the target 510. The first and second lenses may be referred to as collimating lenses or merely lenses. Any suitable lens may be used for the first lens 512 and the second lens 522 such as, but not limited to, geometric and/or refractive lenses fabricated from bulk; flat optics (e.g., diffractive and meta-surface flat optics); and so on.

The first birefringent material 514 may be bonded, or otherwise in proximity, to the first lens 512 and may refract the transmitted beam of light 506. As understood by one of ordinary skill in the art, birefringent materials may have different refractive properties depending on a polarization and/or propagation direction of light. As such, the first birefringent material 514 may refract the transmitted beam of light 506 differently based on a polarization of the transmitted beam of light 506. Additionally, a returned beam of light may be refracted differently than the transmitted beam of light 506. Any material or combination of materials with birefringent properties may be used as the first birefringent material 514 and the second birefringent material 520. The first birefringent material 514 and the second birefringent material 520 may be fabricated from bulk; liquid crystals; meta-surfaces or meta-structures; and so on.

A Faraday rotator 516 may be bonded, or otherwise in proximity, to the first birefringent material 514. Though described as a Faraday rotator, any manner of rotator may be used in accordance with the disclosure. The Faraday rotator 516 may be a polarization rotator and may change a polarization of the transmitted beam of light 506 as the transmitted beam of light 506 moves through the Faraday rotator 516. The Faraday rotator 516 may use a magnet (e.g., a permanent magnet) and/or electromagnetic energy to affect a polarization of the transmitted beam of light 506. The angle of polarization rotation may be calculated by the equation $\beta=VBd$, where $\beta$ is the angle of rotation, V is the Verdet constant for the material of the Faraday rotator 516, B is the magnetic flux density in the direction of propagation, and d is the length of the Faraday rotator 516.

The Faraday rotator 516 may be a non-reciprocal optical element. For example, a beam of light transmit in one direction through the Faraday rotator 516 may be initially rotated 20 degrees clockwise. If the rotated beam is reflected and re-enters the Faraday rotator 516 from the other direction, the initial rotation is not canceled (e.g., the beam of light is not rotated 20 degrees counterclockwise) but may be doubled (e.g., the beam of light is additionally rotated 20 degrees clockwise, such that the complete rotation of the beam of light is 40 degrees clockwise with respect to the transmitted beam of light).

A half-wave plate 518 may be bonded, or otherwise in proximity, to the Faraday rotator 516. The half-wave plate 518 may be any type of wave plate and may affect a polarization of the transmitted beam of light 506. For example, the half-wave plate 518 may have a fast axis of 67.5 degrees. Additionally, other types of wave plates may be used including, but not limited to, a quarter-wave plate or a full-wave plate. Unlike the Faraday rotator 516, the half-wave plate may be reciprocal and may cancel or revert an applied polarization when a beam of light returns through another side of the half-wave plate 518. In some embodiments, the half-wave plate may have an optical axis between 60 degrees and 75 degrees and/or aligned to a polarization of the transmitted beam of light 506. In some embodiments, the half-wave plate may have any optical axis.

The second birefringent material 520 may be formed of the same material or combination of materials as the first birefringent material 514 or may be formed of another material or combination of materials. The second birefringent material 520 may direct the transmitted beam of light 506 along a particular illumination path 506*a* depending on a polarity of the transmitted beam of light 506. A second lens 522 may additionally be provided to focus the transmitted beam of light 506 onto a target 510.

A polarization change of the transmitted beam of light 506 as the transmitted beam of light 506 travels along the illumination path 506*a* will now be described in accordance with the self-mixing interferometry system 500. When the transmitted beam of light 506 is initially emitted from the self-mixing interferometry sensor 502, the transmitted beam of light 506 may have an s-polarization 508*a*. As used herein, the polarization 508*a* may be referred to as a first polarization.

The s-polarization 508*a* may remain consistent (e.g., as s-polarization 508*b*) as the transmitted beam of light 506 travels through the first birefringent material 514 in one propagation direction and when the s-polarization 508*a* is aligned with an extraordinary axis of the first birefringent material 514. That is, an extraordinary ray of the transmitted beam of light 506 may travel through the first birefringent material 514, as refracted, as the s-polarization 508*a* is aligned with the extraordinary axis of the first birefringent material 514. The Faraday rotator 516 and the half-wave plate 518 may act in combination to change the s-polarization 508*b* into a p-polarization 508*c*. This p-polarization 508*c* may remain consistent and may come into contact with the target as p-polarization 508*d*. In this way, the illumination path 506*a* may be altered from the path of the transmitted beam of light 506 through the first birefringent material 514 when the p-polarization 508*c* is aligned with an ordinary axis of the second birefringent material 520. That is, an ordinary ray of the transmitted beam of light 506 may travel through the second birefringent material 520, without refraction, as the p-polarization 508*c* is aligned with the ordinary axis of the second birefringent material 520. Described simply and with reference to FIG. 5A, an extraordinary ray component of the transmitted beam of light 506 is depicted as traveling through the first birefringent component 514 and an ordinary ray component of the transmitted beam of light 506 is depicted as traveling through the second birefringent component 520. As used herein, the polarization 508*d* may be referred to as a second polarization.

Figure 5B:
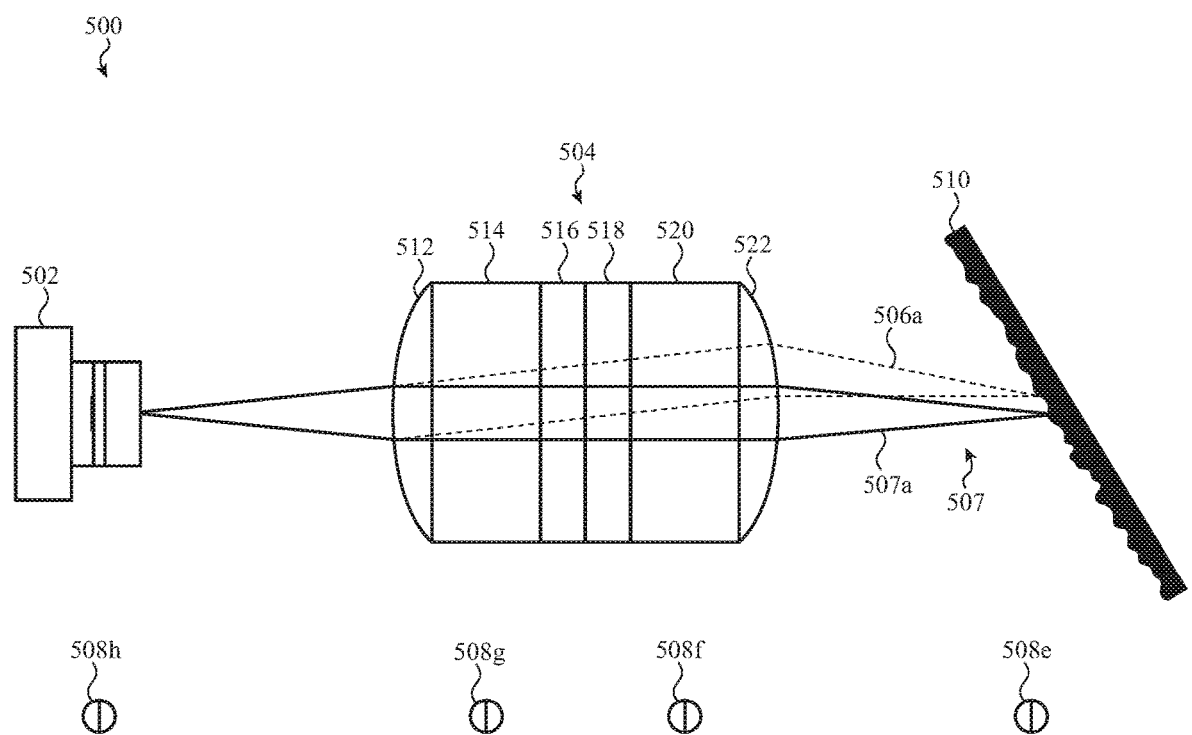
FIG. 5B depicts a beam of light reflected from a target, through a birefringent circulator, and toward a self-mixing interferometry sensor, where the received beam of light has a polarity different from the polarity transmit from the self-mixing interferometry sensor in FIG. 5A.

FIG. 5B depicts the self-mixing interferometry system 500 at an instance after the transmitted beam of light reflects off of the target 510 and returns to the self-mixing interferometry sensor 502 as a returned beam of light 507. The returned beam of light 507 may travel along a collection path 507*a*. The illumination path 506*a* as described with respect to FIG. 5A is depicted in phantom. Identically numbered components present in FIG. 5B are identical to those described herein.

Figure 5C:
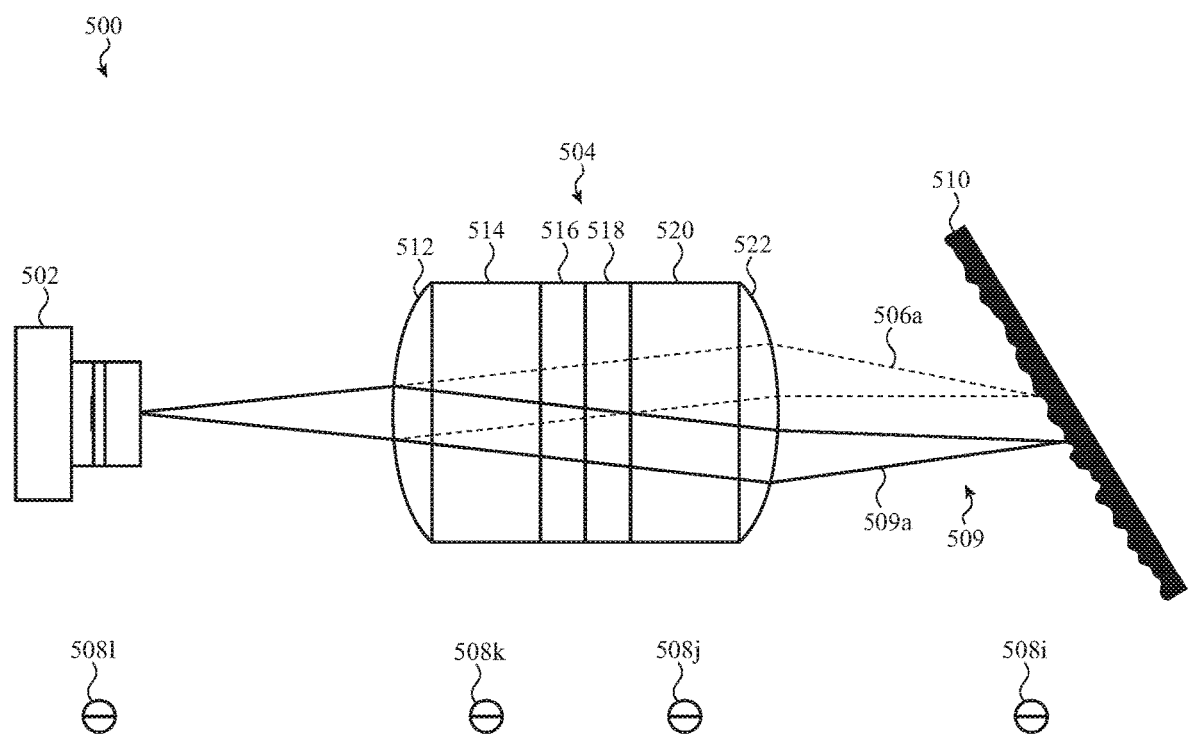
FIG. 5C depicts a beam of light reflected from a target, through a birefringent circulator, and toward a self-mixing interferometry sensor, where the received beam of light has the same polarity as the polarity transmit from the self-mixing interferometry sensor in FIG. 5A.

Once the transmitted beam of light 506 reflects from the target 510, the returned beam of light may comprise light with multiple polarization states from single and multi-pass reflection and light scattering at or below a surface of the target 510. FIG. 5B depicts the component of the returned beam of light 507 with p-polarization 508*e* and FIG. 5C depicts the component of the returned beam of light 509 with s-polarization 508*i*.

In FIG. 5B, the returned beam of light 507 reflects from the target 510 with a p-polarization 508*e*. As the returned beam of light 507 moves along the collection path 507*a*, the polarization stays as p-polarization as it moves through the second birefringent material 520 (e.g., p-polarization 508*f*), the first birefringent material 514 (e.g., p-polarization 508*g*), and as it is received by the self-mixing interferometry sensor 502 (e.g., p-polarization 508*h*). Though the returned beam of light 507 has a p-polarization along each of these markers, the returned beam of light 507 does not necessarily remain at a p-polarization throughout the entirety of the collected path 507*a*. The half-wave plate 518 may shift the polarization of the returned beam of light 507 to a certain degree and this shift may be canceled by the Faraday rotator 516 (see, e.g., FIGS. 6A and 6B). As depicted in FIG. 5B, an ordinary ray component of the returned beam of light 507 does not refract as it moves through the first birefringent material 514 and the second birefringent material 520 as the ordinary ray component is aligned with the ordinary axes of each of the first birefringent material 514 and the second birefringent material 520.

The difference between the illumination path 506*a*, the collection path 507*a*, and the collection path 509*a* may depend on polarization values of light traveling on the paths and a direction of propagation of the light through the birefringent circulator. For example, p-polarization may interact with an ordinary axis of birefringent elements to travel along a certain path. Similarly, s-polarization may interact with an extraordinary axis of birefringent elements to travel along another, at least partially distinct, path. Due to the birefringent properties discussed herein, non-reciprocal optics may be formed.

In some embodiments, a portion of the collection path 507*a* between the self-mixing interferometry sensor 502 and the first lens 512 may fully overlap with a portion of the illumination path 506*a* between the self-mixing interferometry sensor 502 and the first lens 512. In this way, the returned beam of light 507 may return to the self-mixing interferometry sensor 502 with coherent mode/polarization matching with respect to the transmitted beam of light 506.

Both the s-polarization 508*k* and the s-polarization 508*j* may align with the extraordinary axis of both the first birefringent material 514 and the second birefringent material 520. There may therefore be a region at or below a surface of the target 510 where the returned beam of light 506 travels along the collection path 507*a*. This region at or below the surface of the target 510 may be a region of interest and may be a region where properties of or associated with the target 510 are detected.

In FIG. 5C, the returned beam of light 509 reflects from the target 510 with an s-polarization 508*i*. As the returned beam of light 509 moves along the collection path 509*a*, the polarization stays as s-polarization as it moves through the second birefringent material 520 (e.g., s-polarization 508*j*), the first birefringent material 514 (e.g., s-polarization 508*k*), and as it is received by the self-mixing interferometry sensor 502 (e.g., s-polarization 508*l*). Though the returned beam of light 509 has an s-polarization along each of these markers, the returned beam of light 509 does not necessarily remain at an s-polarization throughout the entirety of the collection path 509*a*. The half-wave plate 518 may shift the polarization of the returned beam of light 507 to a certain degree and this shift may be canceled by the Faraday rotator 516 (see, e.g., FIGS. 6A and 6B). Here, it is noted that the self-mixing interferometry sensor 502 may, in some embodiments, only be able to perform self-mixing processes if the polarization of the returned light is identical to the polarization of the transmitted light. In this case, the p-polarization light depicted in FIG. 5B may enter the self-mixing interferometry sensor 502 but may not affect any self-mixing interference process (since light with s-polarization was initially transmit). In some embodiments, a filter may be provided to prevent p-polarized light from entering the self-mixing interferometry sensor 502. The polarization 508*i* may be referred to as a third polarization and the polarization 508*l* may be referred to as a fourth polarization.

Though the illumination and collection paths are depicted with certain boundaries, it is noted that these boundaries are for graphical purposes only. Any illumination or collection path from or to a light source, through a birefringent circulator, and to or from a target may be used in accordance with the present disclosure.

FIGS. 4A-5C generally depict non-confocal illumination and collection paths (e.g., the illumination and collection paths are focused on different locations on the target 410/510). It is understood that this non-confocal arrangement is provided merely for explanatory purposes. Depending on a selection of optical properties of a birefringent circulator and/or self-mixing interferometry sensor, illumination and collection paths may be focused at the same location on a target in a confocal arrangement (e.g., see FIG. 3A).

Figure 6A:
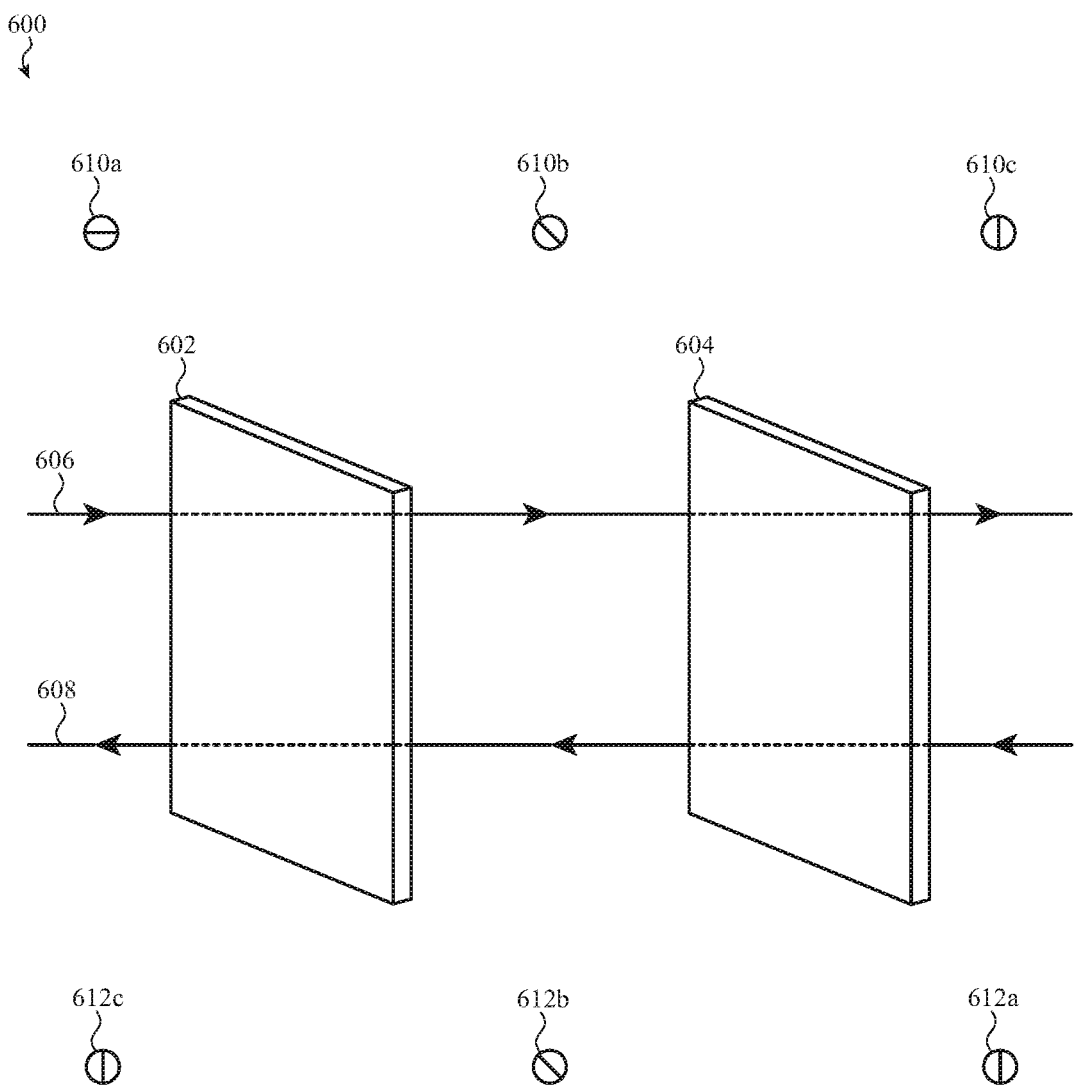
FIG. 6A depicts an optical structure for the non-reciprocal treatment of light.
Figure 6B:
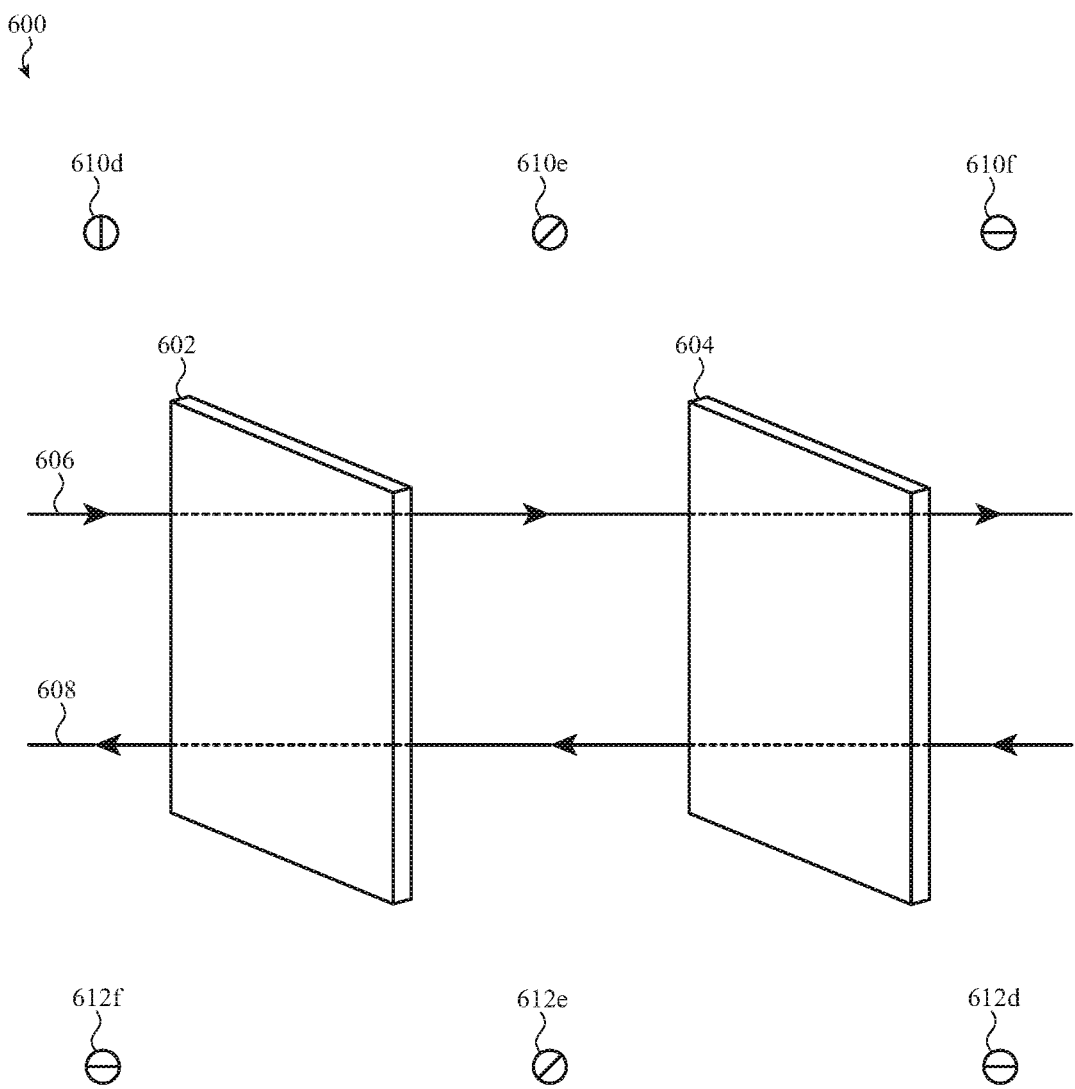
FIG. 6B depicts an optical structure for the non-reciprocal treatment of light, where the transmitted light has a polarization different from a polarization of the light transmit in FIG. 5A.

FIGS. 6A and 6B depict an optical structure 600 for the non-reciprocal treatment of light polarization. The optical structure 600 depicted in FIGS. 6A and 6B may be equivalent, or largely similar to, the Faraday rotator, wave plates, and/or other forms of optics or optical circulators discussed with reference to FIGS. 1A-5C. As described herein, the optical structure 600 may be used in accordance with a non-reciprocal self-mixing interferometry system. In order to change a polarization of light, a Faraday rotator 602 may be provided along with a wave plate 604. The Faraday rotator 602 and the wave plate 604 may be aligned so that a beam of light passes through each successively.

In the example depicted in FIG. 6A, a first beam of light 606 may initially have an s-polarization 610a, though the polarization is not limited to such. As the first beam of light 606 travels through the Faraday rotator 602, a polarization of the first beam of light 606 may be rotated in a clockwise or counterclockwise direction (e.g., a clockwise direction is depicted in FIG. 6A). The polarization at this stage may be an angled polarization 610b between s-polarization and p-polarization states. The angled polarization 610b may be angled at any angle depending on properties of the Faraday rotator 602. The beam of light 606 with the angled polarization 610b may then pass through the wave plate 604. The wave plate 604 may further rotate the polarization of the beam of light 606 so that the beam of light 606 has a p-polarization 610c after passing through the wave plate 604. In this way, a p-polarized beam of light may be converted to an s-polarized beam of light.

A beam of light 608 may propagate in a direction opposite to the direction of propagation of the beam of light 606. When traveling in the opposite direction, the beam of light 608 may first pass through the wave plate 604 before passing through the Faraday rotator 602. In this direction, the wave plate 604 may initially shift the polarization of an initial p-polarization 612a of the beam of light 608 into an angled polarization 612b. Here, it is noted that the polarization of the beam of light 606 at polarization state 610b and the polarization of the beam of light 608 at polarization state 612b may be the same, though the two polarization states may be different in other embodiments. However, as the beam of light 608 travels through the Faraday rotator 602, rather than transforming to an s-polarization state (e.g., state 610a) as originally present in the beam of light 606, the beam of light 608 may transition to a p-polarization state 612c. In this way, non-reciprocal optics 600 may affect polarization states differently depending on a direction of propagation for a beam of light.

Though the polarizations 610b and 612b are displayed at an approximate 45-degree angle, it should be understood that any polarization angle may be used in accordance with the provided disclosure. The degree of polarization rotation of the Faraday rotator 602 and/or the wave plate 604 may be any amount and any associated optical properties may be provided.

In the example depicted in FIG. 6B, a first beam of light 606 may initially have a p-polarization 610d, though the polarization is not limited to such. As the first beam of light 606 travels through the Faraday rotator 602, a polarization of the first beam of light 606 may be rotated in a clockwise or counterclockwise direction (e.g., a clockwise direction is depicted in FIG. 6B). The polarization at this stage may be an angled polarization 610e between s-polarization and p-polarization states. The angled polarization 610e may be angled at any angle depending on properties of the Faraday rotator 602. The beam of light 606 with the angled polarization 610e may then pass through the wave plate 604. The wave plate 604 may further rotate the polarization of the beam of light 606 so that the beam of light 606 has an s-polarization 610f after passing through the wave plate 604.

A beam of light 608 may propagate in a direction opposite to the direction of propagation of the beam of light 606. Thus, the beam of light 608 may first pass through the wave plate 604 before passing through the Faraday rotator 602. In this direction, the wave plate 604 may initially shift the polarization of an initial s-polarization 612d of the beam of light 608 into an angled polarization 612e. Here, it is noted that the polarization of the beam of light 606 at polarization state 610e and the polarization of the beam of light 608 at polarization state 612e may be the same, though the two polarization states may be different in other embodiments. However, as the beam of light 608 travels through the Faraday rotator 602, rather than transforming to a p-polarization state (e.g., state 610d) as originally present in the beam of light 606, the beam of light 608 may transition to an s-polarization state 612f. In this way, non-reciprocal optics 600 may affect polarization states differently depending on a direction of propagation.

In some embodiments, therefore, a beam of light transmit in one direction may shift to an orthogonal polarization while a beam of light transmit in an opposite direction may remain at the same polarization.

In the above examples, the Faraday rotator 602 may always rotate a beam of light in the same direction, regardless of a direction of propagation or incident polarization. For example, the Faraday rotator 602 may always rotate a polarization of a beam of light in a clockwise direction. This may result in a non-reciprocal environment where an initial polarization shift cannot be reversed simply by traveling back through the Faraday rotator 602 (e.g., the polarization shift is increased rather than reversed). The wave plate 604 may be a reciprocal optic and may rotate a polarization of a beam of light in a different direction depending on a direction of propagation of a beam of light. Therefore, the wave plate 604 may undo or reverse an initial polarization shift if the shifted beam of light returns through the wave plate 604. Though depicted as a plate in FIGS. 6A and 6B, the Faraday rotator 602 and the wave plate 604 may include other shapes and may be formed from one optical component or multiple optical components (e.g., a number of lenses, magnets, and materials). For example, the Faraday rotator 602 and the wave plate 604 may be shaped as a tube formed from different materials.

Figure 7:
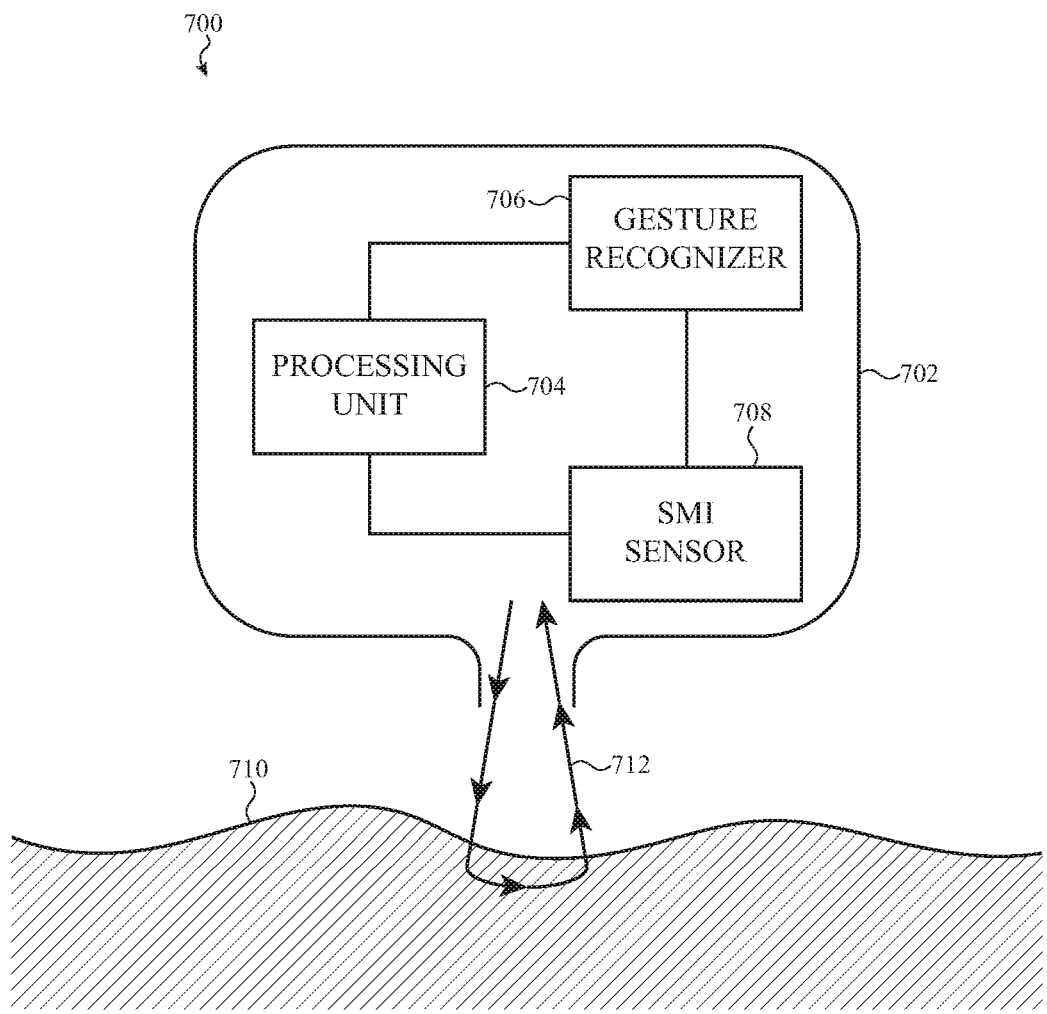
FIG. 7 depicts an example embodiment of a gesture recognition system using non-reciprocal self-mixing interferometry.

FIG. 7 depicts an example embodiment of a gesture recognition system 700 using a self-mixing interferometry (SMI) sensor 708 such as, for example, discussed with reference to SMI sensors and associated optics in FIGS. 1A-6B. As discussed herein, the self-mixing interferometry sensor 708 may be provided with non-reciprocal optics to transmit and receive beams of light along different optical paths. In the embodiment depicted here, the non-reciprocal optics may be incorporated into the self-mixing interferometry sensor 708, though in alternate embodiments the non-reciprocal optics may be positioned within an opening of an electronic device 702.

As discussed here, the self-mixing interferometry sensor 708 may emit and receive beams of light 712. The beams of light 712 may be directed toward a target 710. The target 710 may be a body part of a user such as a wrist or hand. The beams of light 712 may partially penetrate the target 710 so that sub-surface features (e.g., veins) are measured.

The electronic device 702 may additionally include a processing unit 704 and a gesture recognizer 706. The gesture recognizer 706 may work in conjunction with the processing unit 704 to store self-mixing interferometry signals associated with a certain gesture. In some embodiments, the processing unit 704 may be integrated with the gesture recognizer 706.

As described herein, the electronic device 702 may be operated in a training mode where a user makes a number of gestures in response to a displayed gesture indication graphic. As the user makes the indicated gesture, self-mixing interferometry signals may be stored within the gesture recognizer and may be associated with a particular gesture. A gesture recognized by the processing unit 704 may be accepted as a valid input command and may affect an operation of the electronic device 702. In some embodiments, systems of a self-mixing interferometry system may detect changes in operational parameters of the SMI sensor 708, may apply a frequency domain analysis to the operational parameter, and may map or otherwise determine the gesture of the user by detected properties of the operational parameter as determined by the frequency domain analysis. As a non-limiting example, an operational parameter may be a voltage or current change of the SMI sensor 708.

Figure 8A:
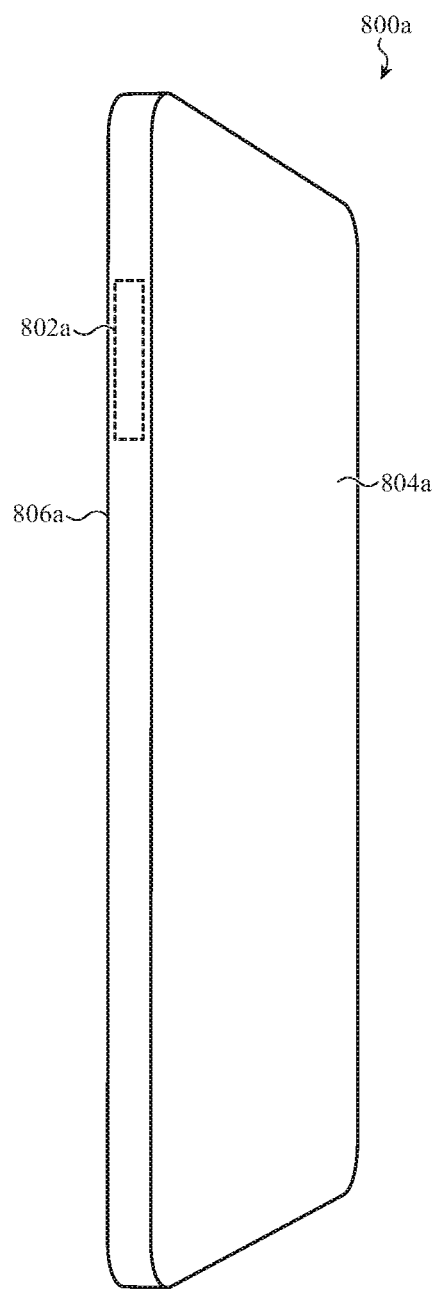
FIG. 8A depicts an example non-reciprocal self-mixing interferometry sensor incorporated into a mobile phone.
Figure 8B:
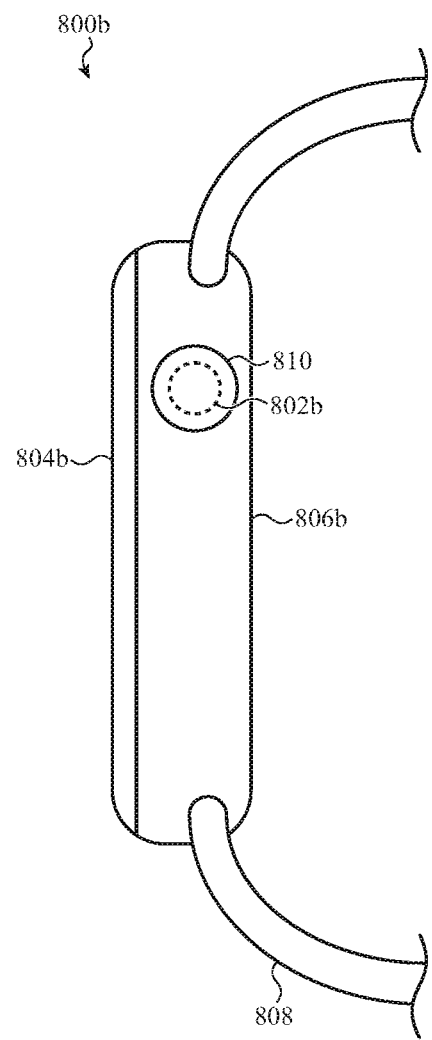
FIG. 8B depicts an example non-reciprocal self-mixing interferometry sensor incorporated into an electronic watch.
Figure 8C:
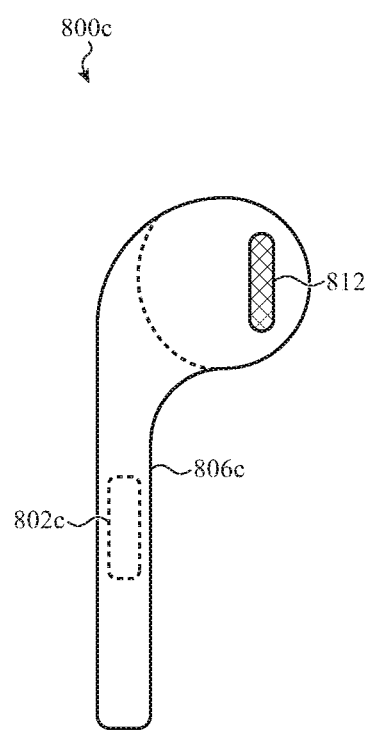
FIG. 8C depicts an example non-reciprocal self-mixing interferometry sensor incorporated into an earbud.

FIGS. 8A-8C depict example electronic devices in which a self-mixing interferometry sensor may be incorporated. These example electronic devices are intended to be merely explanatory and are not intended to be exclusive.

FIG. 8A depicts a mobile phone 800a including a display 804a, a self-mixing interferometry sensor 802a, and a housing 806a. The housing 806a may include an opening and may surround a portion of the display 804a. The self-mixing interferometry sensor 802a may utilize sensed self-mixing signals to determine the presence or motion of a part of a user (e.g., a user's finger). For example, a user may swipe her finger across the self-mixing interferometry sensor 802a to turn the mobile phone 800a on or off. In some embodiments, a user may place her finger on top of the self-mixing interferometry sensor 802a where sub-dermal measurements (e.g., a heartbeat measurement) may be collected.

Any of the self-mixing interferometry sensors, and associated optics and/or circulators, discussed with reference to FIGS. 1A-7 may be integrated with the mobile phone 800a, for example, a self-mixing interferometry sensor designed to measure detected properties of sub-surface features underneath, for example, a user's skin and/or of features on or above a target.

For example, a self-mixing interferometry sensor 802a may be used as a biometric sensor and may be configured to detect a user's blood flow. In additional or alternative embodiments, a self-mixing interferometry sensor 802a may be used to measure a surface roughness of a target (e.g., a skin surface or an inanimate object such as a wall, table, or aluminum can) and/or a particle density or detected particles (e.g., a concentration of smoke in the air). A self-mixing interferometry sensor 802 may additionally or alternatively be capable of measuring detected properties of any provided object and may, for example, treat a particular object or speed of an object as an input (e.g., a swipe may turn on or off the mobile phone 800a) when the object is either in contact with the mobile phone 800a or not in contact with the mobile phone 800a.

FIG. 8B depicts an electronic watch 800b including a display 804b, a self-mixing interferometry sensor 802b, a housing 806b, a digital crown 810, and a strap 808. The strap may connect the electronic watch 800b with an arm of a user. The digital crown 810 may be rotatable and may be used to detect an input. In some embodiments, the digital crown 810 may be immovable. The self-mixing interferometry sensor 802b may utilize self-mixing interferometry to detect a presence or motion of an object to detect, for example, a swipe. In some embodiments, the self-mixing interferometry sensor 802b may be provided underneath the electronic watch 800b to capture measurements from a user's wrist while the electronic watch 800b is being worn.

Any of the self-mixing interferometry sensors, and associated optics and/or circulators, discussed with reference to FIGS. 1A-7 may be integrated with the electronic watch 800b, for example, a self-mixing interferometry sensor designed to detect the detected properties of sub-surface features underneath, for example, a user's skin and/or of features on or above a target.

In some embodiments, the self-mixing interferometry sensor 802b may be focused at a point beneath a user's skin and may be configured to detect, for example, a blood flow and/or a blood oxygenation level. In additional or alternative examples, a self-mixing interferometry sensor 802b may be directed to emit light to a point on a user's skin, the light may follow a "banana path" underneath a user's skin, and the light may return back out of the user's skin at another point before being returned to the self-mixing interferometry sensor 802b. By performing self-mixing analyses on the returned light, properties of sub-dermal features may be obtained. In additional or alternative examples, a self-mixing interferometry sensor 802b may be used as a gesture sensor and may be able to detect a user's gesture.

FIG. 8C depicts an earbud 800c including a housing 806c, a self-mixing interferometry sensor 802c, and a speaker 812. The earbud 800c may be designed to fit within a user's ear to provide a sound via the speaker 812. The self-mixing interferometry sensor 802c may be provided as an input detector and may detect the speed of a finger to change a volume of sound output from the speaker 812 and/or an operation state of the earbud 800c. In some embodiments, the self-mixing interferometry sensor 802c may capture information about a user's ear canal structure and other biometric features such as a user's breathing, swallowing, speaking, and so on.

Any of the self-mixing interferometry sensors, and associated optics and/or circulators, discussed with reference to FIGS. 1A-7 may be integrated with the earbud 800c, for example, a self-mixing interferometry sensor designed to detect the detected properties of sub-surface features underneath, for example, a user's skin and/or of features on or above a target.

A self-mixing interferometry sensor 802c integrated within an earbud 800c may be used, for example, to detect a skin movement and/or gesture of a user. By measuring a gesture, an input to the earbud 800c may be detected such as, for example, a volume control or an on/off operation. In some embodiments, a self-mixing interferometry sensor 802c may measure detected properties of a user's skin and may, for example, increase or decrease the volume when a user is in motion, as determined by a change in skin shape.

Figure 9:
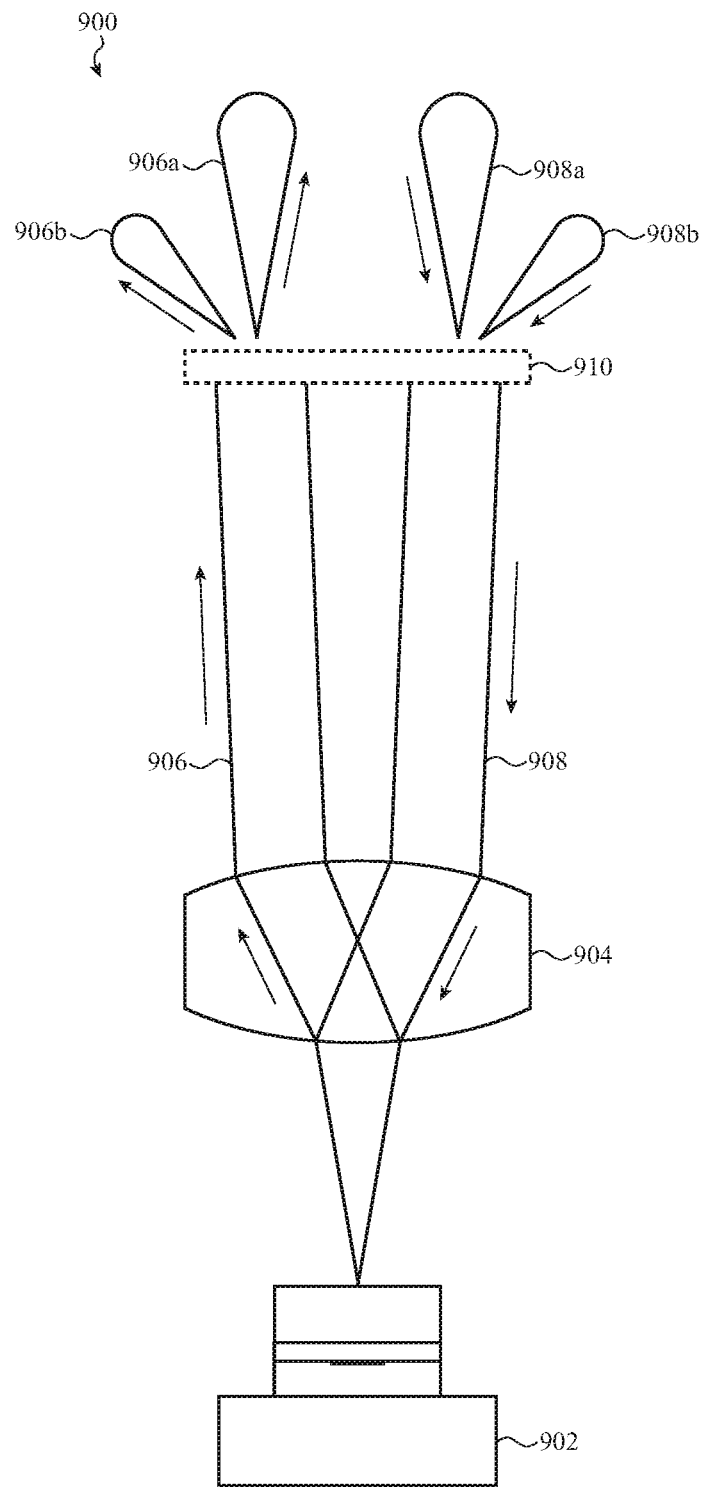
FIG. 9 depicts a self-mixing interferometry sensor including a non-reciprocal path for preventing overlapping side lobe interference for an optical phase array.

FIG. 9 depicts a self-mixing interferometry system 900 with beam scanning and/or shaping capabilities as a system for preventing side lobe interference. The system as depicted in FIG. 9 may use any of the self-mixing interferometry systems or sensors, along with associated non-reciprocal optics, discussed with respect to FIGS. 1A-8C.

In systems without birefringent optics, a beam of light transmit to and/or returned at an optical phase array may result in an overlap between main lobes and side lobes emitted through the optical phase array. This may result in side lobe interference.

In the self-mixing interferometry system 900, birefringent optics 904, such as described herein, may be used so that main lobes of transmitted and returned light overlap (e.g., to meet at a point of interest) while side lobes do not overlap so as to prevent side lobe interference. In the depicted embodiment, a transmitted beam of light 906 is directed toward an optical phase array 910 as may be used for scanning and/or aiming beams of light. After passing through the optical phase array 910, the transmitted beam of light 906 may be separated into a transmitted main lobe 906a and a transmitted side lobe 906b. The transmitted side lobe 906b may be aimed away from the target of interest while the transmitted main lobe 906a may be directed toward the target of interest (e.g., a target where self-mixing interferometry is performed). Returned light may be reflected toward the optical phase array 910 as both a returned main lobe 908a and a returned side lobe 908b. The returned main lobe 908a may overlap with the transmitted main lobe 906a and may include light reflected from the target of interest. The returned side lobe 908b may be light reflected from surfaces other than the target of interest. The returned main lobe 908a and the returned side lobe 908b may be filtered through the optical phase array 910 and may be directed back through the birefringent optics 904 and the self-mixing interferometry sensor 902. In this way, side lobe interference from an unwanted target and between the transmitted side lobe 906b and the returned side lobe 908b may be eliminated or reduced.

In some embodiments, the self-mixing interferometry system 900 may be used in coherent spatial scanning operations. As used herein, coherent spatial scanning may refer to optical coherence tomography (OCT) and may be used to collect three-dimensional images of an object (e.g., a tissue or other physical object). The self-mixing interferometry system 900 may scan or pulse the self-mixing interferometry sensor 902 across an object, may collect reflected light, and may perform self-mixing operations to convert a received signal into an image. As understood by one of ordinary skill in the art, OCT may be used to perform three- or two-dimensional imaging analysis of sub-dermal features (e.g., sub-dermal organs). In some embodiments, the self-mixing interferometry system 900 may be used for far-field three-dimensional scanning and may be referenced as light detection and ranging (LIDAR).

Though the optical phase array 910 is depicted as one unit, any number of units is possible. For example, one optical phase array may be provided for the transmitted beam of light 906 and a second optical phase array may be provided for the returned beam of light 908.

Figure 10:
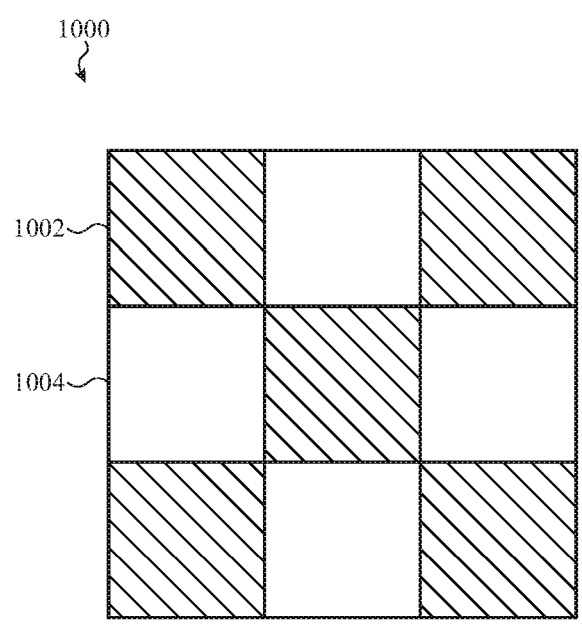
FIG. 10 depicts a birefringent meta-structure as a non-reciprocal optical element.

FIG. 10 depicts an example passive non-reciprocal element 1000. The system as depicted may use any of the self-mixing interferometry systems or sensors, along with associated non-reciprocal optics, discussed with respect to FIGS. 1A-9. The passive non-reciprocal element 1000 may be a birefringent meta-structure and may include different orientations of chiral elements so that permanent magnets and/or biased electric or magnetic fields are not required (e.g., as may be required in a Faraday rotator). A first chiral element 1002 may polarize a wave in a first direction (e.g., clockwise). The first chiral element 1002 may reflect a wave propagating in a second direction opposite from the first direction. A second chiral element 1004 may be a mirror-image of the first chiral element 1002 so that a wave is polarized in a second direction while being reflected in the first direction. The first chiral element 1002 and the second chiral element 1004 may be formed in a grid-like pattern as depicted in FIG. 10 and may function as a non-reciprocal meta-surface mimicking Faraday rotation, such as described herein. As such, the passive non-reciprocal element 1000 may replace the Faraday rotators as described with respect to the above described embodiments.

As described above, one aspect of the present technology is measuring surface or sub-surface property on surfaces or objects. As such, personal information data, including heart rate, BMI, blood oxygenation level, location-based data, data or records relating to a user's health or level of fitness (e.g., vital signs measurements, medication information, exercise information), or any other identifying or personal information may be measured.

The present disclosure recognizes that the use of such personal information data, in the present technology, can be used to the benefit of users. For example, the personal information data can be used to provide health recommendations and history that are tailored to and/or derived from the user. Further, other uses for personal information data that benefit the user are also contemplated by the present disclosure. For instance, fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities implement and consistently use privacy policies and practices that are generally recognized as meeting or exceeding industry or governmental requirements for ensuring personal information data is kept private and secure. Such policies should be easily accessible by users, and should be updated as the collection and/or use of data changes. Personal information from users should be collected for the legitimate and reasonable uses of the entity and should not be shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, sleep patterns may be provided based on non-personal information data or a bare minimum amount of personal information, such as events or states of the device associated with a user, other non-personal information, or publicly available information.

Other examples and implementations are within the scope and spirit of the disclosure and appended claims. For example, self-mixing interferometers may be used on fitness monitors, in wearable electronics, and in other pressure sensing/measuring systems. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An apparatus for performing non-reciprocal self-mixing interferometry, the apparatus comprising:
    a self-mixing interferometry sensor having a light source configured to emit a beam of light; and
    a birefringent circulator positioned over an aperture of the light source and configured to direct the beam of light emitted by the light source along an illumination path, the birefringent circulator comprising:
        a Faraday rotator; and
        a wave plate, wherein the Faraday rotator and the wave plate are configured to transform a first polarization of the beam of light into a second polarization as the beam of light travels along the illumination path, wherein:
    the birefringent circulator directs a returned portion of the beam of light, received along a collection path different from the illumination path, back toward the light source.

2. The apparatus of claim 1, wherein the Faraday rotator and the wave plate are configured to keep a third polarization of the returned portion of the beam of light unchanged as the returned portion of the beam of light is directed back toward the light source.

3. The apparatus of claim 1, wherein the wave plate is a half-wave plate with an optical axis aligned to the first polarization.

4. The apparatus of claim 1, wherein a first angle of the beam of light, as the beam of light leaves the birefringent circulator along the illumination path, is different than a second angle of the returned portion of the beam of light, as the returned portion of the beam of light enters the birefringent circulator along the collection path.

5. The apparatus of claim 1, wherein:
    the self-mixing interferometry sensor emits the beam of light having p-polarization before the beam of light enters the birefringent circulator; and
    the birefringent circulator is configured to cause the beam of light to have s-polarization after the beam of light exits the birefringent circulator.

6. The apparatus of claim 5, wherein:
    the birefringent circulator is configured to receive the returned portion of the beam of light having p-polarization as the returned portion of the beam of light enters the birefringent circulator; and
    the birefringent circulator is configured to cause the returned portion of the beam of light to have p-polarization after the returned portion of the beam of light exits the birefringent circulator.

7. The apparatus of claim 1, wherein:
    the birefringent circulator has a first refractive index in a first direction of travel along the illumination path;
    the birefringent circulator has a second refractive index in a second direction of travel along the collection path; and
    the first refractive index is different from the second refractive index.

8. The apparatus of claim 1, wherein the birefringent circulator focuses the illumination path on a common detection space.

9. An electronic device for performing non-reciprocal self-mixing interferometry, the electronic device comprising:

a self-mixing interferometry sensor configured to emit a beam of light; and a birefringent circulator positioned in an illumination path of the emitted beam of light and in a collection path of a returned portion of the beam of light, the birefringent circulator configured to direct the beam of light emitted from the self-mixing interferometry sensor from a first aperture of the birefringent circulator, the birefringent circulator comprising:

a Faraday rotator; and a wave plate, wherein the Faraday rotator and the wave plate are configured to transform a first polarization of the beam of light into a second polarization as the beam of light travels along the illumination path, wherein:

the birefringent circulator directs the returned portion of the beam of light, received from a second aperture of the birefringent circulator, into the self-mixing interferometry sensor.

10. The electronic device of claim 9, wherein: the birefringent circulator is configured to direct the beam of light to a first location on a target; and the birefringent circulator is configured to receive the returned portion of the beam of light from a second location on the target.

11. The electronic device of claim 9, further comprising a processing unit configured to determine, from an output of the self-mixing interferometry sensor, a displacement or a movement of a sub-surface feature of an object.

12. The electronic device of claim 11, wherein the processing unit is configured to:

apply a frequency domain analysis to the self-mixing interferometry signal; and determine the displacement or the movement of the sub-surface feature of the object based on a change in at least one property of an operational parameter of the self-mixing interferometry signal, as determined by the frequency domain analysis.

13. The electronic device of claim 9, wherein the electronic device is at least one of an electronic watch or a mobile phone.

14. An electronic device, comprising:

a self-mixing interferometry sensor, comprising:

a light emitter configured to emit a beam of light; and a photodetector configured to receive a returned portion of the beam of light; and a set of one or more optical components positioned over an aperture of the light emitter and comprising a first birefringent wedge, a second birefringent wedge and a Faraday rotator positioned between the first birefringent wedge and the second birefringent wedge, the one or more optical components defining:

a first optical path configured to propagate the emitted beam of light between a first receiving location and a first emission location; and a second optical path configured to propagate the returned portion of the beam of light between a second receiving location and a second emission location, wherein the first optical path is different from the second optical path.

15. The electronic device of claim 14, wherein the set of one or more optical components further comprises a lens configured to collimate the beam of light as the beam of light enters the set of one or more optical components.

16. The electronic device of claim 14, wherein the set of one or more optical components further comprises a half-wave plate positioned between the Faraday rotator and the second birefringent wedge.

17. The electronic device of claim 14, wherein the set of one or more optical components is a passive, non-reciprocal meta-structure.

* * * * *